(12) United States Patent
Kousai et al.

(10) Patent No.: US 10,156,511 B2
(45) Date of Patent: Dec. 18, 2018

(54) OPTICAL SENSOR, ANALYZER AND ANALYSIS METHOD

(71) Applicant: Kabushiki Kaisha Toshiba, Minato-ku, Tokyo (JP)

(72) Inventors: Shouhei Kousai, Yokohama Kanagawa (JP); Kaita Imai, Tokyo (JP); Yosuke Akimoto, Yokohama Kanagawa (JP)

(73) Assignee: Kabushiki Kaisha Toshiba, Tokyo (JP)

(*) Notice: Subject to any disclaimer, the term of this patent is extended or adjusted under 35 U.S.C. 154(b) by 0 days.

(21) Appl. No.: 15/456,658

(22) Filed: Mar. 13, 2017

(65) Prior Publication Data

US 2017/0268982 A1 Sep. 21, 2017

(30) Foreign Application Priority Data

Mar. 15, 2016 (JP) .................................. 2016-051028

(51) Int. Cl.
| | |
|---|---|
| *G01N 15/14* | (2006.01) |
| *C12M 1/00* | (2006.01) |
| *C12M 1/34* | (2006.01) |
| *G01N 33/483* | (2006.01) |
| *G01N 15/10* | (2006.01) |

(52) U.S. Cl.
CPC ......... *G01N 15/1436* (2013.01); *C12M 31/02* (2013.01); *C12M 41/06* (2013.01); *C12M 41/46* (2013.01); *G01N 33/4833* (2013.01); *G01N 15/1456* (2013.01); *G01N 15/1468* (2013.01); *G01N 2015/1006* (2013.01)

(58) Field of Classification Search
CPC ..................... G01N 15/1436; G01N 15/1456
USPC .................... 356/335–344, 300–334
See application file for complete search history.

(56) References Cited

U.S. PATENT DOCUMENTS

| | | | |
|---|---|---|---|
| 5,347,122 | A | 9/1994 | Ansorge et al. |
| 8,372,629 | B2 | 2/2013 | Southern et al. |
| 2004/0201835 | A1* | 10/2004 | Coates ............... G01N 21/31 356/73 |
| 2008/0145925 | A1 | 6/2008 | Sakai et al. |
| 2008/0266653 | A1 | 10/2008 | Korpinen et al. |
| 2010/0096563 | A1 | 4/2010 | Ponjee et al. |
| 2011/0116091 | A1* | 5/2011 | Shibayama ............ G01J 3/02 356/334 |
| 2011/0136165 | A1 | 6/2011 | Vojnovic et al. |
| 2012/0224053 | A1 | 9/2012 | Vykoukal et al. |
| 2012/0288920 | A1 | 11/2012 | Takeda |
| 2013/0278928 | A1* | 10/2013 | Mourey ............ G01N 21/274 356/301 |
| 2015/0219545 | A1 | 8/2015 | Gurkan et al. |
| 2015/0293012 | A1 | 10/2015 | Rapoport et al. |

FOREIGN PATENT DOCUMENTS

| | | |
|---|---|---|
| JP | 05-505457 A | 8/1993 |
| JP | 2006-246720 A | 9/2006 |
| JP | 2008-505628 A | 2/2008 |

(Continued)

*Primary Examiner* — Tri T Ton
(74) *Attorney, Agent, or Firm* — White & Case LLP

(57) ABSTRACT

According to one embodiment, an optical sensor includes a plurality of sensing parts two-dimensionally arranged in a matrix to form a sensor surface, and a phototransmissive sample-supporting plate arranged to be opposed to the sensing parts.

6 Claims, 29 Drawing Sheets

(56) References Cited

FOREIGN PATENT DOCUMENTS

| | | |
|---|---|---|
| JP | 2010-028289 A | 2/2010 |
| JP | 2011-0198083 A | 10/2011 |
| JP | 2015-029461 A | 2/2015 |
| JP | 2015-535593 A | 12/2015 |

\* cited by examiner

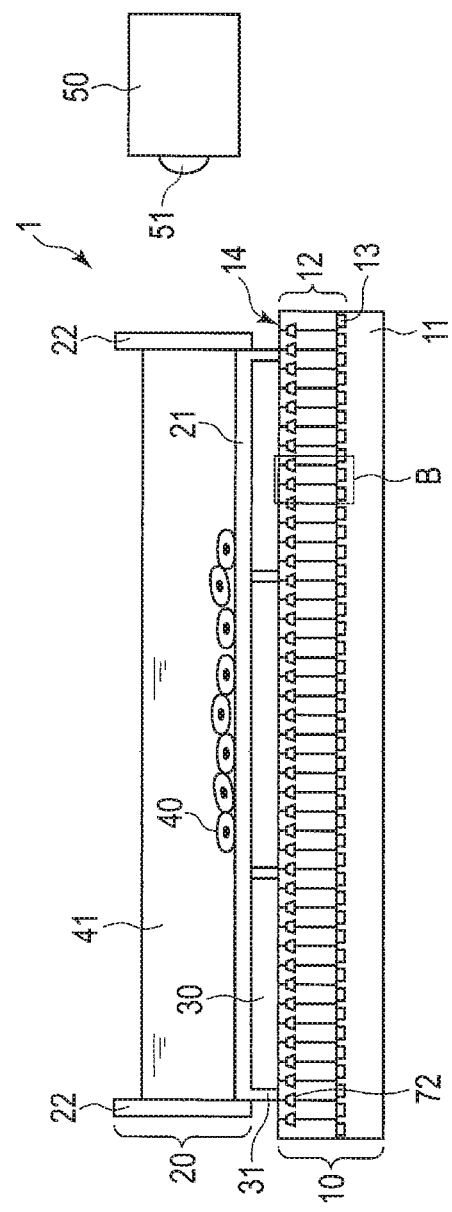
F I G. 10A

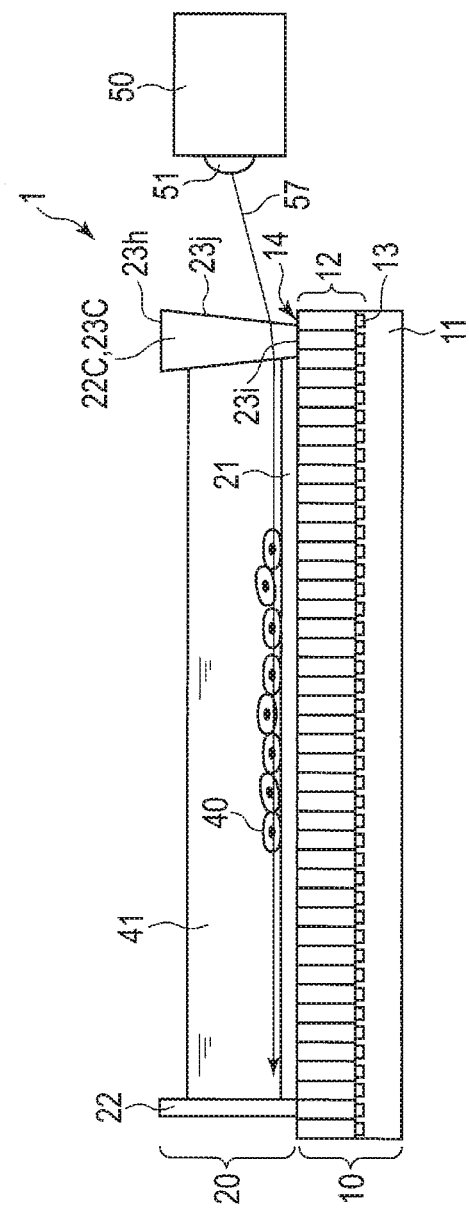
F I G. 11C

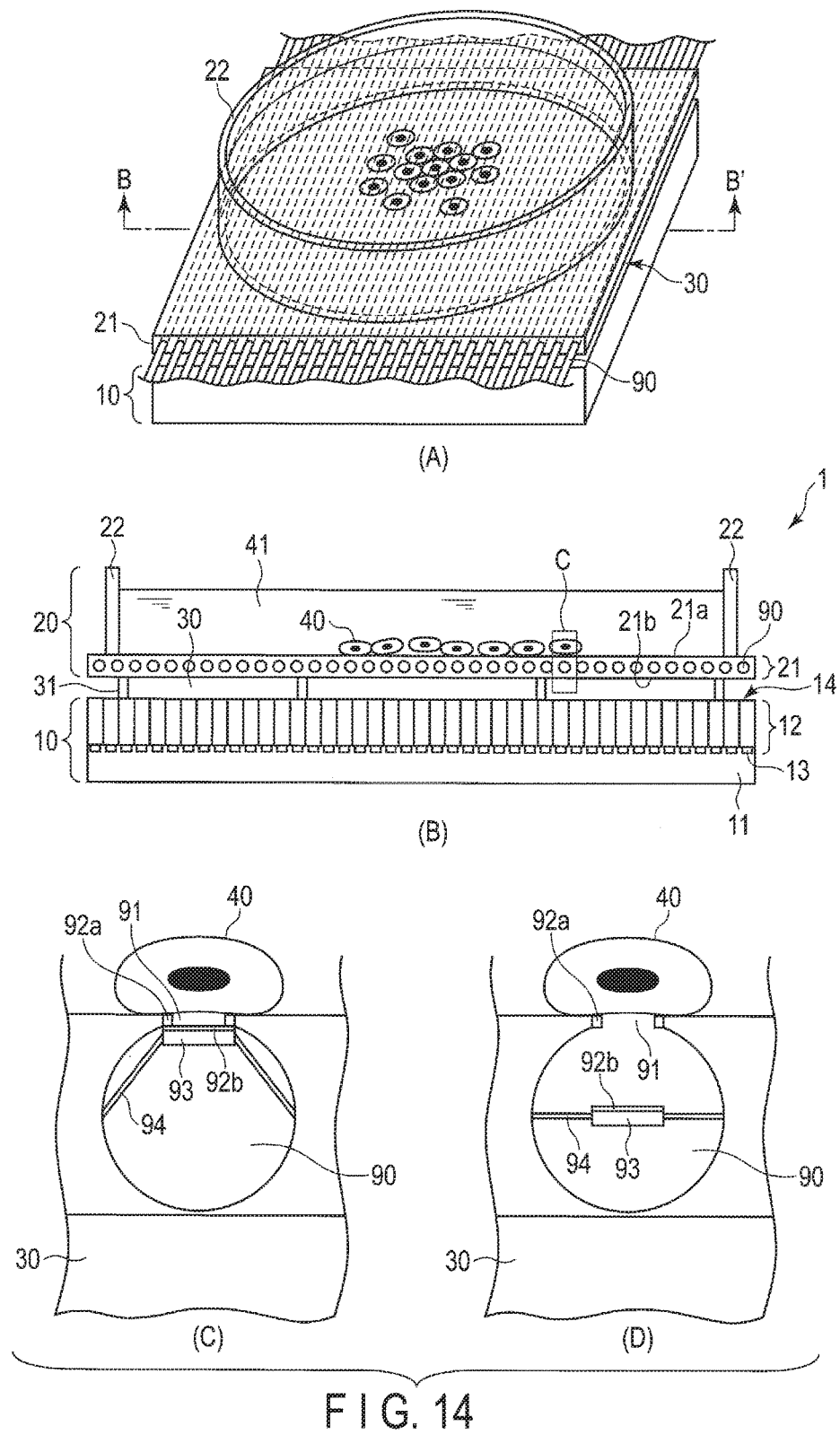
F I G. 14

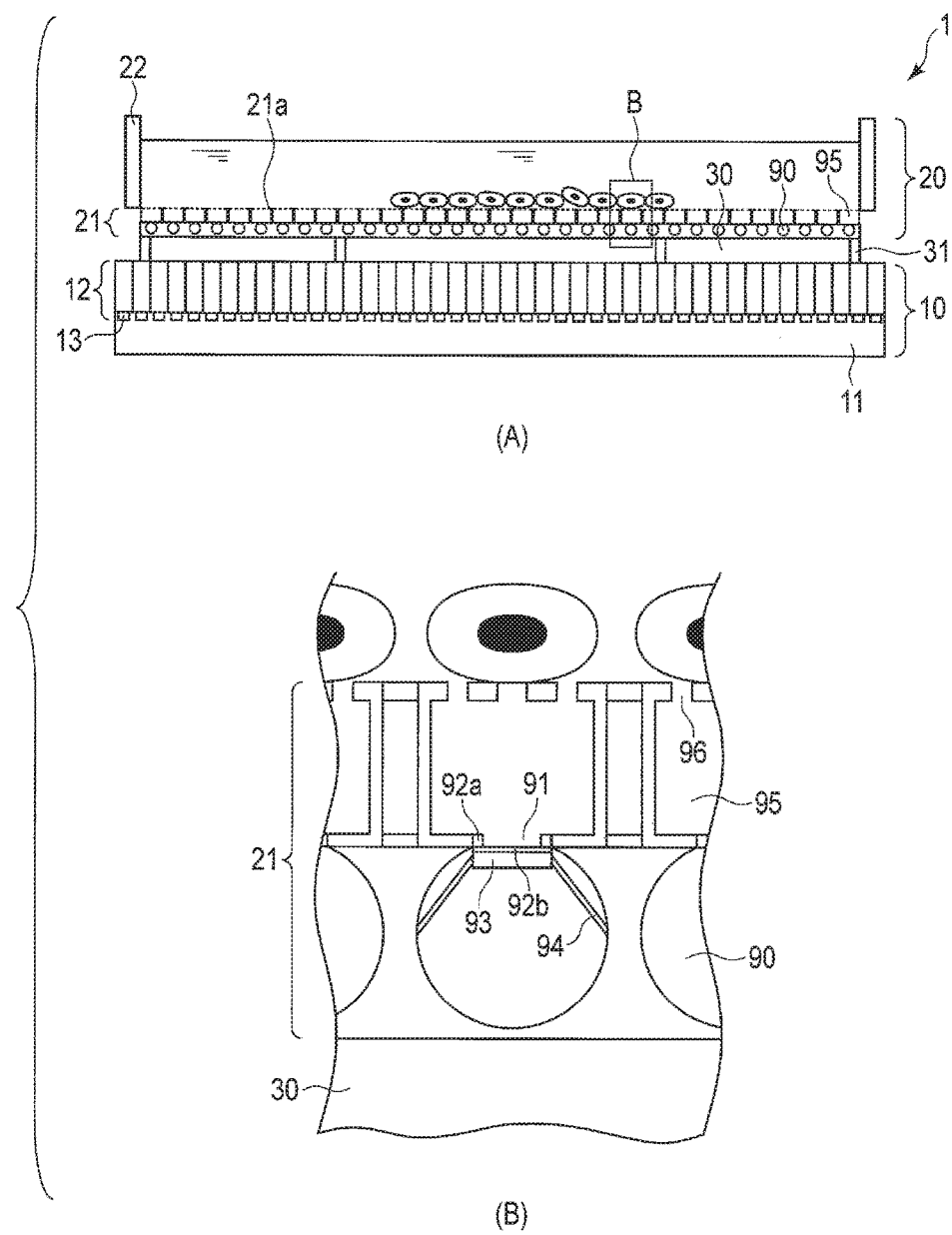
F I G. 15

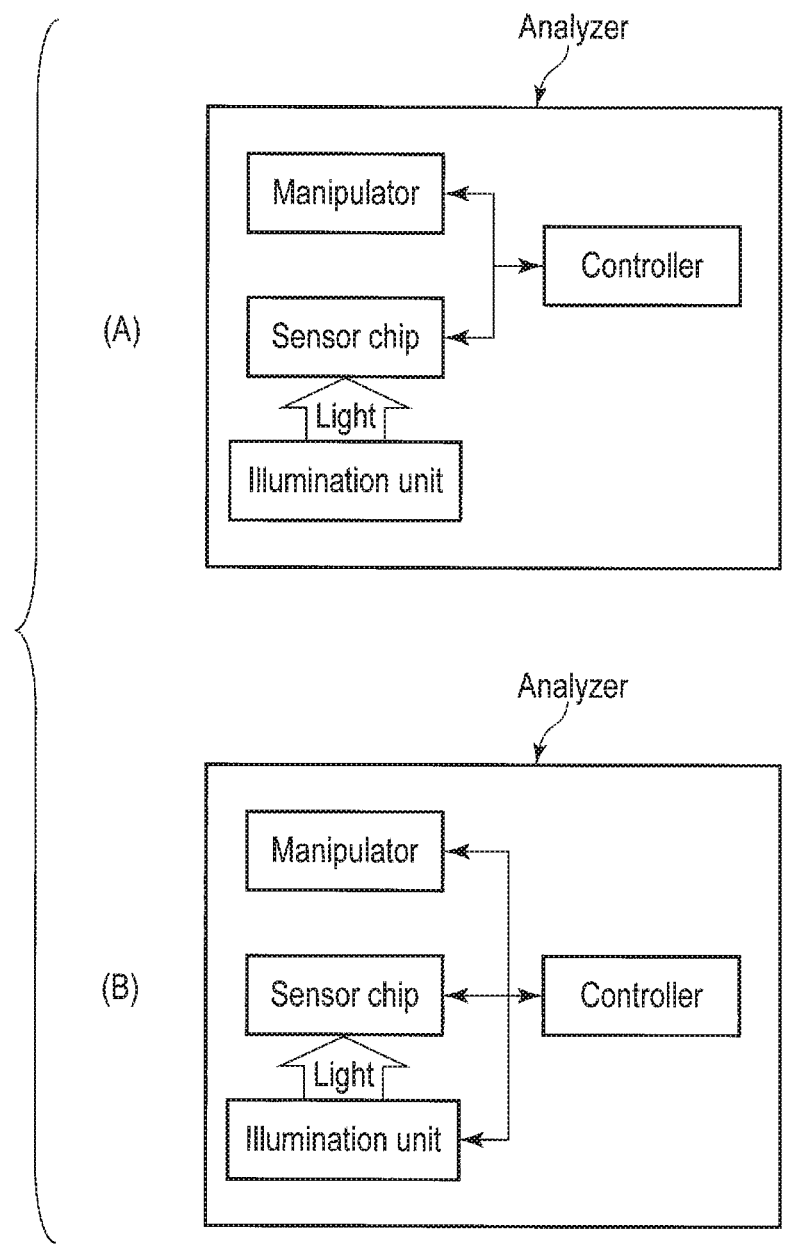
F I G. 18

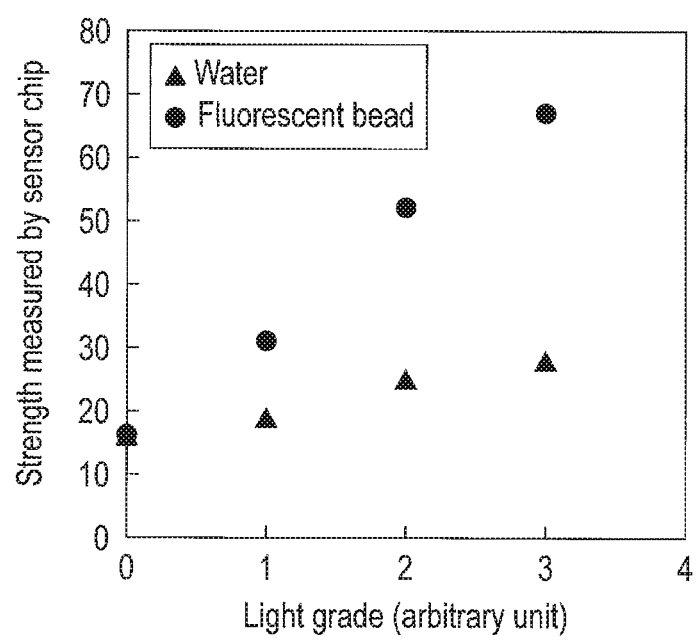
F I G. 26

OPTICAL SENSOR, ANALYZER AND ANALYSIS METHOD

CROSS-REFERENCE TO RELATED APPLICATIONS

This application is based upon and claims the benefit of priority from Japanese Patent Application No. 2016-051028, filed Mar. 15, 2016, the entire contents of which are incorporated herein by reference.

FIELD

Embodiments described herein relate generally to an optical sensor, analyzer and analysis method.

BACKGROUND

To achieve a society in which people can live more healthily and comfortably, studies have been conducted to discover causes and onset mechanisms of diseases and to find preventative and treatment methods for such diseases. By acquisition and analysis of information revealed through studies about diseases and about individual onset factors, reduction of onset risks of the diseases is proposed.

As an approach to achieve the above society, there is a technique to obtain data of diseases by analyzing bio samples. Many kinds of optical devices have been developed to analyze biological samples. Such devices are, for example, a flow cytometry device and a cell sorter, in which cells are flown into channels for the analysis.

Under such circumstances, further development of devices for biological sample analysis is demanded.

BRIEF DESCRIPTION OF THE DRAWINGS

FIG. 10A is a cross-sectional view of an example of an optical sensor of a fifth embodiment.

FIG. 11C is a cross-sectional view of an example of the optical sensor of the sixth embodiment during its operation.

FIG. 14 shows an example of an optical sensor of a ninth embodiment.

FIG. 15 is a cross-sectional view showing an example of an optical sensor of the ninth embodiment.

FIG. 18 is a block diagram showing an example of an analyzer of an embodiment.

FIG. 26 shows a result of measurement obtained in the example.

DETAILED DESCRIPTION

Figure 1:
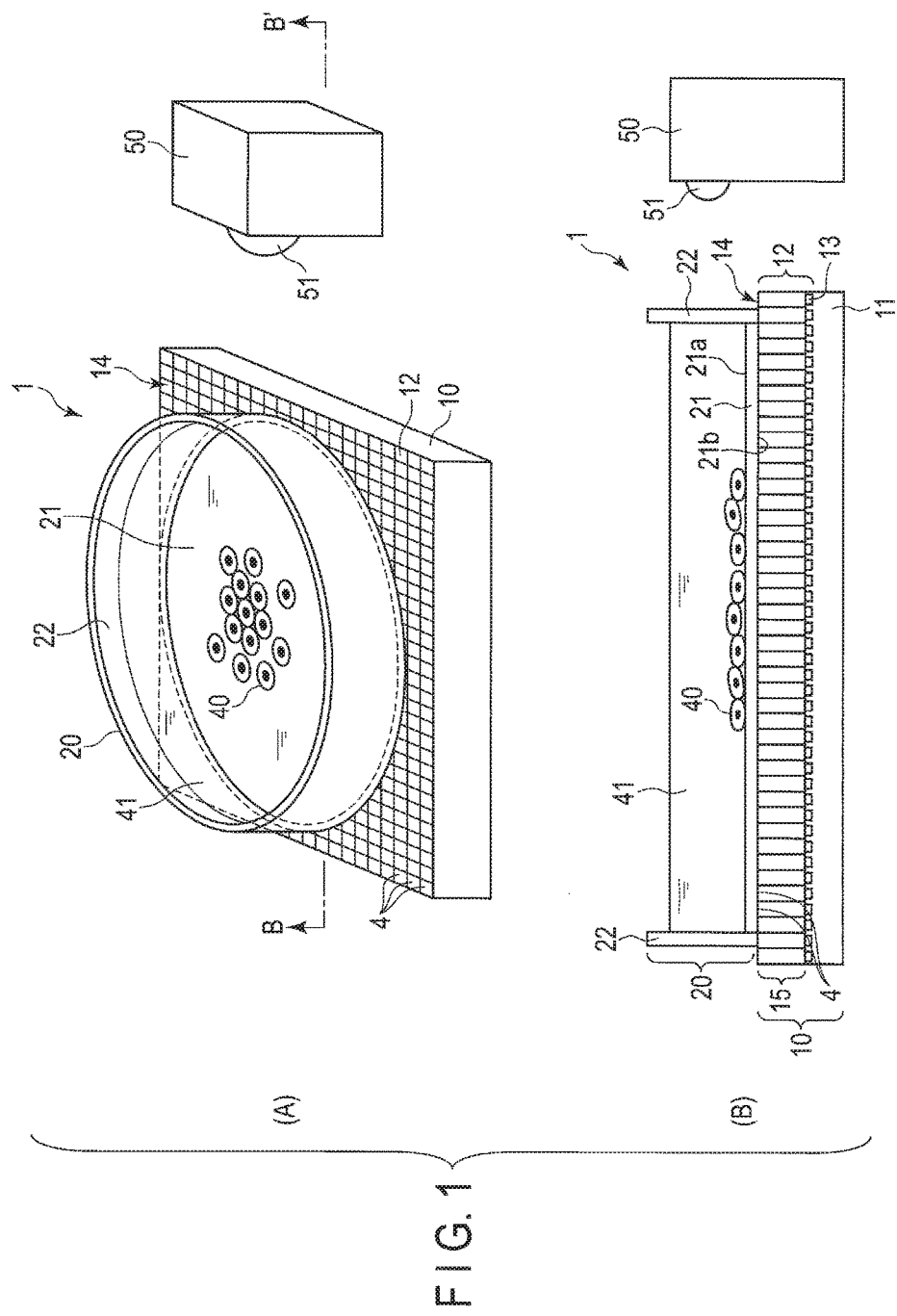
FIG. 1 shows an example of an optical sensor of a first embodiment.

In general, according to one embodiment, an optical sensor includes a plurality of sensing parts arranged in a matrix in a two-dimensional region to form a sensor surface, and phototransmissive sample-supporting plate arranged to face the sensor surface.

According to another embodiment, an optical sensor includes a plurality of sensing part arranged in a matrix two-dimensional region to form a sensor surface, and a sample container having a phototransmissive bottom arranged to face the sensor surface.

The optical sensor two-dimensionally detects optical data from content, that is, a sample contained in the sample container. Through sensing, information about the sample contained in the sample container or information about a target to be analyzed in the sample can be obtained.

Hereinafter, embodiments will be explained with reference to accompanying drawings. Depictions therein are schematic and may differ from dimensions to be actually adopted.

First Embodiment

FIG. 1(A) is a perspective view of an example of an optical sensor of an embodiment. FIG. 1(B) is a cross-sectional view of the optical sensor of FIG. 1(A), taken along line B-B'. The optical sensor 1 of FIG. 1(A) and FIG. 1(B) includes a semiconductor sensor chip 10, sample container 20, and light source 51.

The semiconductor sensor chip 10 is a main body of the optical sensor and performs two-dimensional sensing of light. The semiconductor sensor chip 10 includes a substrate 11 and a plurality of sensing parts 13. The sensing parts 13 are arranged in a matrix in a two-dimensional region on the substrate 11. In other words, the sensing parts 13 form vertical and horizontal lines of desired numbers on the two-dimensional region.

The sensing parts 13 are disposed to face upward, that is, to face the surface side of the semiconductor sensor chip 10. Thus, for example, the sensing parts 13 perform two-dimensional sensing of light from the sample container 20 above the semiconductor sensor chip 10. The semiconductor sensor chip 10 of FIG. 1 includes phototransmissive members 15 above the sensing parts 13. The phototransmissive members 15 are used as a part of a light passage. Thus, light entering the surface of the phototransmissive members 15 passes through the phototransmissive members 15, and reaches the sensing parts 13. The light reaching the sensing parts 13 is sensed by the sensing parts 13.

As detailed later, the sensing parts 13 are arranged not to interfere each other in sensing of the light. For example, a via and/or an interconnection may be arranged in the region of the phototransmissive member 15 between adjacent sensing parts 13 to prevent the interference.

With the sensing parts 13 arranged as above, the surface of the semiconductor sensor chip 10 functions as a sensor surface 14. The sensor surface 14 corresponds to, in the example of the optical sensor of FIG. 1, the upper surface of the phototransmissive member 15. The sensor surface 14 includes a part of surface of the phototransmissive member 15 corresponding to each sensing part 13 as a sub-sensor surface 4. The arrangement of the sub-sensor surfaces 4 corresponds to the arrangement of the sensing parts 13, and as a whole, the outline of the sensor surface 14 matches the outline of the two-dimensional region in which the sensing parts 13 are arranged in a matrix. Thus, the outline of the sensor surface 14 and the outline of the two-dimensional region can have the same dimension and shape. A via (which is not shown) may further be located between adjacent sub-sensor surfaces.

In the following description, the part which includes one sensing part and extends from upper end of the substrate 11 reaching the sensor surface 14 is referred to as an optical sensor element 12. However, this is only an example, and in some embodiments, for instance, optical sensor element 12 may be arranged independently, or may be unintegrated from adjacent optical sensor elements, or may be integrated with other optical sensor elements except for the sensing parts therein. In the example of FIG. 1, the solid lines between the optical sensor elements 12 are drawn for convenience of depiction of the arrangement of optical sensor elements 12 and do not mean that members defining each optical sensor element 12 are necessary therein. The same applies to other cross sectional views of the optical sensors.

The sample container 20 includes a bottom 21 and a wall 22. Both the bottom 21 and the wall 22 are formed of a phototransmissive material. In the example of FIG. 1, the bottom 21 is a circle and the wall 22 extends upward from the position enclosing cylindrical surface of surrounding the bottom 21. In this example, the wall 22 vertically contacts the bottom 21. Furthermore, the wall 22 contacts the bottom 21 in a liquid tight manner such that the sample container 20 can maintain a liquid therein.

Between the semiconductor sensor chip and the sample container, the lower surface of the bottom 21 is fixed to face the sensor surface provided by the sensing part 13.

In FIG. 1(A) and FIG. 1(B), the optical sensor with a sample contained in the sample container 20 is depicted. The sample depicted here includes, for example, a cell keeping solution 41 and cells 40 which are a target included therein.

The light source 51 is disposed to emit light from the outside of the sample container 20 into the inside thereof through the wall 22. In FIG. 1(A) and FIG. 1(B), the light source 51 provided with an illumination unit 50 is depicted for example. When using the optical sensor, the light from the light source 51 passes through the wall 22 and the cell keeping solution 41 in the sample container 20 and is irradiated onto cells 40. The light from cells 40 pass through the bottom 21 and the sensor surface located with facing the bottom 21, and reaches the sensing parts 13.

In the above example, the wall 22 extends upward from the cylindrical surface of the bottom 21. In other examples, the wall 22 may extend upward on the upper surface of the bottom 21 to enclose a desired region thereon.

The present embodiment presents an optical sensor which can obtain optical information about the target to be analyzed in a simpler manner.

Furthermore, for example, with such a structure, information about the target to be analyzed under a specific conditions can be obtained more easily. Hereinafter, each component of the optical sensor will be explained in detail.

1. Semiconductor Sensor Chip

As described above, the semiconductor sensor chip 10 includes a plurality of sensing parts 13 arranged in a matrix in a two-dimensional region on the substrate 11.

The substrate 11 functions as a base on which the sensing parts 13 are disposed or formed in matrix. The substrate 11 is, for example, a semiconductor substrate. For example, the substrate may be a semiconductor substrate formed of silicon. The main surface of the substrate may be, for example, 1×1 mm to 30×30 mm, however, not being limited there to. The thickness of the substrate, for example, may be 10 to 700 μm.

Figure 2:
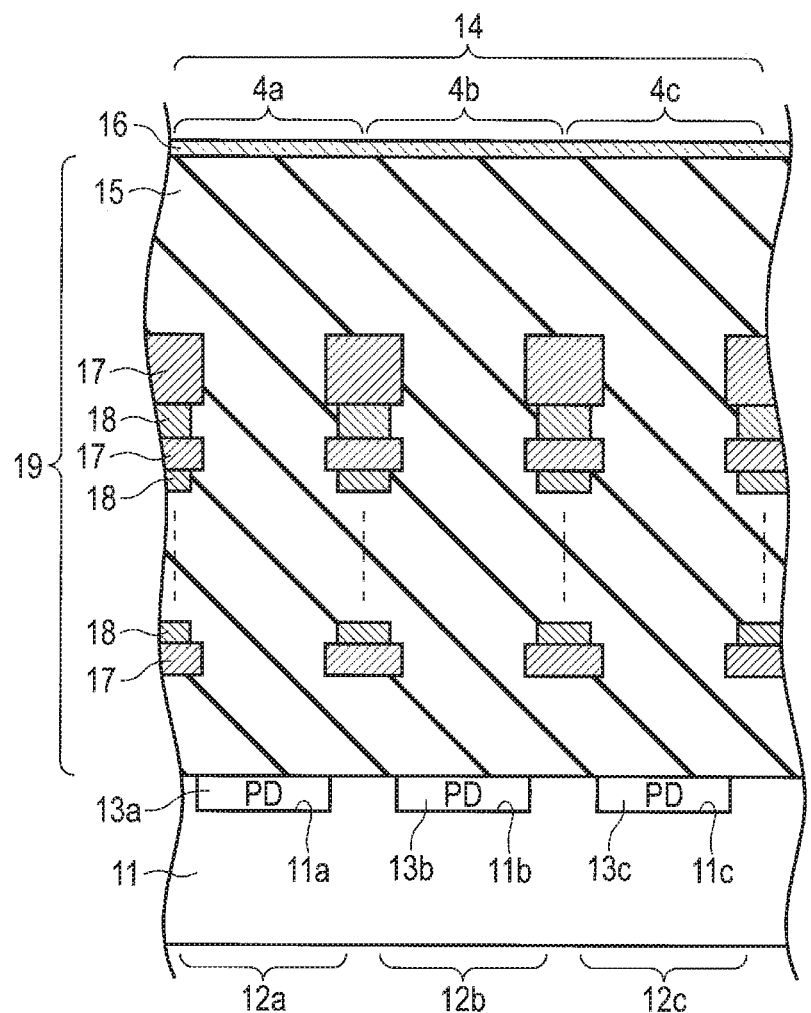
FIG. 2 is an enlarged cross-sectional view of an optical sensor element of the first embodiment.

The sensing parts 13 may be arranged in the optical sensor element 12 as above. The optical sensor element 12 is now explained with reference to FIG. 2. The optical sensor element 12 is an example of an optical sensor element which can be included in the embodiment shown FIG. 1. FIG. 2 shows three optical sensor elements 12a, 12b and 12c included in a semiconductor sensor chip to be adjacent to each other, as being viewed in an enlarged manner. Three sensor elements include sensing parts 13a, 13b and 13c in recesses 11a, 11b and 11c on the upper surface of the substrate 11.

The sensing parts 13 may be, for example, any publically known photoreceptor element used for photo-detection. The sensing part is, for example, a photodiode.

The sensing parts 13 are arranged on the substrate 11 to be embedded and at least partly exposed thereon such that they can sense the light. An $SiO_2$ film 15 is on the sensing parts 13 as a phototransmissive member 15. In the $SiO_2$ film 15, a monolayer or multilayer of interconnection(s) 17 may be disposed to transfer optical data detected by the sensing parts 13. The interconnections 17 may be electrically connected to each other with vias 18 formed of a conductive material. In such a structure, the interconnections 17 block stray light from adjacent optical sensor elements and the light coming directly from the above each of sensor elements can efficiently be received by each of the sensing parts 13. A layer including the SiO$_2$ film 15, interconnections 17 and vias 18 is referred to as an interconnection layer 19. The optical sensor elements 12a, 12b, and 12c further include a protective layer as an upper layer of the phototransmissive member 15. The protective layer is formed of, for example, a phototransmissive material used for protection of the surface of the semiconductor sensor chip. The protective layer is, for example, a silicon nitride film 16. The optical sensor elements 12a, 12b and 12c of FIG. 2 have sub-sensor surfaces 4a, 4b and 4c which are the upper surface of the silicon nitride film 16. They may form a sensor surface 14. In FIG. 2, the sensor surface 14 extends to the part omitted by wave lines.

The semiconductor sensor chip 10 including such optical sensor elements 12 as in FIG. 2 is formed through a method now explained below.

The semiconductor sensor chip 10 can be formed by forming a plurality of optical sensor elements 12 integrally on the substrate 11. To form the semiconductor sensor chip 10, a semiconductor process is used, for example. Initially, impurities are shot to the parts on the substrate 11, where sensing parts 13 are to be formed. Thereby, the sensing parts 13 are formed, and thereon, a SiO$_2$ film 15 is deposited. During the deposition of the SiO$_2$ film, interconnections 17 are formed with vias 18 connecting at desired positions. A silicon nitride film 16 may be deposited on the surface of the SiO$_2$ film 15 by, for example, a CVD method.

Since the semiconductor sensor chip 10 is structured as above, optical data of the light reaching to the sensing parts 13 therein can be obtained. The light may be, for example, visible light, ultraviolet light, infrared light, fluorescence, phosphorescence or luminescence. As in FIG. 1, the sensing parts 13 are arranged in a matrix on the substrate 11. Thus, when analyzing a target using the optical sensor of the embodiment, two-dimensional positional data of the sensing parts 13 can be associated with the optical data obtained by the sensing parts 13.

In a single semiconductor sensor chip, approximately one hundred to one hundred million sensing parts 13 may be included; however, not being limited thereto. The number of sensing parts 13 can be adjusted by a type, size and quantity of cells or image resolution to be achieved. By providing the plurality of sensing parts 13, the semiconductor sensor chip 10 provides a sensor surface 14 as its surface.

The size of a sensing part may be, for example, 500×500 nm to 10×10 μm; however, no limitation is intended thereby. The size of sensing part 13 can be determined based on, for example, a type, quantity and size of a sample or a target contained in the sample container 20 or image resolution to be achieved.

The size of an optical sensor element is, for example, 500×500 nm to 10×10 μm; however, not being limited thereto. The size of an optical sensor element can be determined based on, for example, a type, quantity and size or image resolution to be achieved. The height of an optical sensor element is, for example, a few micrometers, that is, 1 μm to 4 μm; however, not being limited thereto. A pitch between optical sensor elements is, for example, 0.3 μm to 30 μm; however, not being limited thereto.

In some embodiments, the optical sensor element 12 may be an optical sensor element with a publically-known optical sensor. Such an optical sensor is, for example, a CMOS image sensor, CCD image sensor, or single photon avalanche diode (SPAD) image sensor, which converts a signal of light detected by photodiodes to electric signal or thermopile sensor converts a signal of light detected by thermocouple to an electric signals.

In the above example, the silicon nitride film 16 is provided with the phototransmissive member 15 as a surface protective layer. Instead of a silicon nitride film 16, however, a silicon oxide film, aluminum oxide film or tantalum oxide film may be used as a protective layer, or a surface protective layer may not be disposed on the surface of the phototransmissive member. Furthermore, the phototransmissive member may be formed below the sensing parts 13. In that case, a protective layer may be formed on the surface of the sensing parts 13. For example, if the sensing parts 13 are on the surface of the substrate 11, the interconnection layer 19 may be disposed between the substrate 11 and the sensing parts 13. In such a structure, optical data of the light reached to the sensing parts 13 can be acquired.

2. Sample Container

As described above, the sample container includes the wall 22 and the bottom 21 as in FIG. 1(A) and FIG. 1(B).

In the embodiment of FIG. 1(A), the main surface of the bottom 21 is planer member whose main surface is circle. However, the main surface of the bottom may be, for example, a polygon such as a quadrangle, rectangle or square. The wall 22 rises from for example the circumference of the bottom 21 to surround the entirety of the upper surface 21a of the bottom 21. Thus, the wall 22 is a cylinder in FIG. 1(A). If the shape of the main surface of the bottom 21 is a polygon, the wall may be a polyangular cylinder. Alternatively, the wall 22 may rise to surround a part of the upper surface 21a of the bottom 21. In that case, the wall 22 is, for example, a cylinder, elliptical cylinder, or polyangular cylinder. In the example of FIG. 1(A), the wall 22 rises vertically from the bottom 21; however, the wall 22 does not necessarily rise vertically with respect to the bottom 21, and the wall 22 may rise substantially vertically or may rise obliquely.

The bottom 21 and the wall 22 are formed of a phototransmissive material which transmits, for example, visible light, ultraviolet light, infrared light, fluorescence, phosphorescence or chemical/biological/biochemical luminescence. Such a material is, for example, glass, silicon dioxide, polystyrene, PDMS or the like. The bottom 21 and the wall 22 may be formed of the same material, or may be formed of different materials.

The thickness of the bottom 21, that is, a distance between the upper and lower main surfaces of the bottom 21 is, for example, 10 nm to 2 mm, however, not being limited thereto. The thickness of the wall 22, that is, the thickness extending outward of the sample container 20 parallel to the lower surface 21b of the bottom 21 is, for example, 10 nm to 2 mm, or 50 μm to 2 mm, however, not being limited thereto. The thickness of the wall 22 need not be constant through the whole region. Such a case occurs, for example, when the wall 22 is a polyangular cylinder and at least one of sides in whole is thicker than the other side. If the wall 22 is a cylinder, it may be formed such that, the wall 22 has thickness, the thickness of a desired region of the wall 22 can be thicker than another region, the desired region being the region corresponding to an arc having desired length in the circle shape in the cross-section given when the cylinder is cut in a direction perpendicular to the cylinder axis. The bottom 21 and the wall 22 may have the same thickness or may have different thicknesses. The height of the wall 22 is, for example, 50 μm to 10 mm, however, not being limited thereto. A gap between two points opposed on the circumference of the bottom 21 is, for example, 100 μm to 30 mm, however, not being limited thereto.

Alternatively, a commercially available petridish, plate, or multiwell plate formed of glass, polyethylene or polystyrene may be used entirely or partly of the sample container 20. In that case, the bottom surface of the sample container 20 and the sensor surface of the semiconductor sensor chip are fixed to be opposed to each other to form the optical sensor as in the embodiment.

With the sample container structured as above, information about a target to be analyzed in a specific condition can be obtained. The target to be analyzed in a specific condition is, for example, living cells in culture condition of which changes by being extracted from a culture medium, or cells culture of which requires a gaseous environment of a particular concentration. The sample container provides a field where light can be irradiated onto such a target.

The semiconductor sensor chip 10 and the sample container 20 structured as above may be fixed such that the sensing parts 13 and the bottom 21 of the sample container 20 are opposed to each other. The semiconductor sensor chip 10 and the sample container 20 structured as above may be fixed such that the lower surface 21b of the bottom 21 and the sensor surface 14 are adhered to each other. However, the lower surface 21b and the sensor surface 14 may be fixed with a gap formed therebetween, as explained later.

The optical sensor 1 can be manufactured by forming the semiconductor sensor chip 10 and then, fixing the bottom 21 of the sample container 20, which is formed independently, on the upper part of the semiconductor sensor chip 10. Alternatively, the optical sensor 1 can be manufactured by forming the semiconductor sensor chip 10 and the bottom 21 of the sample container 20 integrally through a semiconductor process and fixing thereto the wall 22 which is formed separately or injection-molding the wall 22 on the bottom 21. Fixation of the parts is achieved by, for example, an adhesive agent. The adhesive agent is, for example, PDMS (silicone resin), epoxy resin or the like.

In some embodiments, the semiconductor sensor chip 10 and the sample container 20 may be detachably attached.

3. Light Source

The light source 51 is arranged externally to emit light in the sample container through the wall. The light source 51 is, for example, disposed in the illumination unit 50 as in FIG. 1. The light source 51 may emit, for example, visible light such as red light, green light, blue light and white light or ultraviolet light or infrared light or any combination of two or more of the aforementioned light types. The light source 51 is, for example, an organic electroluminescent source, LED or laser which can emit the above types of light. The light source may be or may not be fixed to the semiconductor sensor chip. If the light source is not fixed to the semiconductor sensor chip, it may be a light source which is provided in a lighting device and emits the above types of light. Such a lighting device is disposed in, for example, an incubator, chamber, or darkroom.

Second Embodiment

Figure 3:
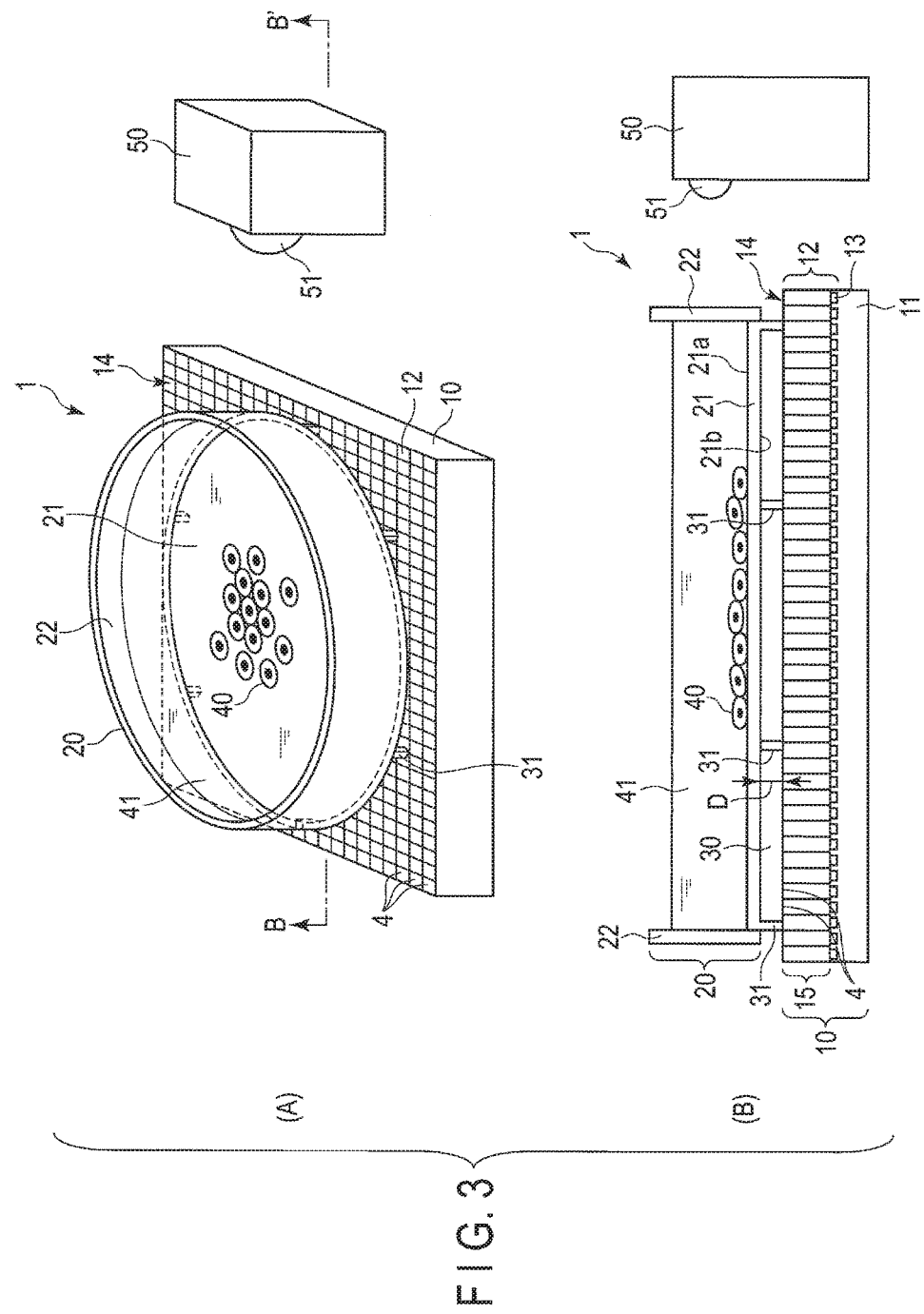
FIG. 3 shows an example of an optical sensor of a second embodiment.

FIGS. 3(A) and 3(B) show a preferable embodiment. FIG. 3(A) is a perspective view of an example of the optical sensor including a low-refractive-index layer 30 between the sensor surface 14 and the bottom 21 which are face each other. FIG. 3(B) is a cross-sectional view of the optical sensor of FIG. 3(A), taken along line B-B'. The low-refractive-index layer 30 possesses a refractive index which is lower than that of the bottom 21. The material possessing lower-refractive-index layer 30 is, for example, vacuumed, or filled with a material the refractive index of which is lower than that of the bottom 21. Such a material may be, for example, air or a meta-material. The low-refractive-index layer 30 may be formed by, for example, a plurality of supporting members 31 used to create a gap between the sensor surface 14 and the bottom 21. The supporting member 31 is shaped as a circular pillar rod or a prism rod, one end of which is fixed to the sensor surface 14 and the other end of which is fixed to the lower surface of the bottom. The height of the supporting member 31 can be determined to correspond to a gap between the sensor surface 14 and the bottom 21 of the low-refractive-index layer. The maximum length on the cross-section of the supporting member 31 may be determined such that a desired low-refractive-index layer 30 can be formed and maintained between the sensor surface 14 and the bottom 21 and optical data of a sample can be detected properly. The maximum length of the supporting member 31 may be, for example, 100 μm to 10 mm. The supporting member 31 may be formed of, for example, $SiO_2$, glass, PDMS, or epoxy resin.

Figure 4:
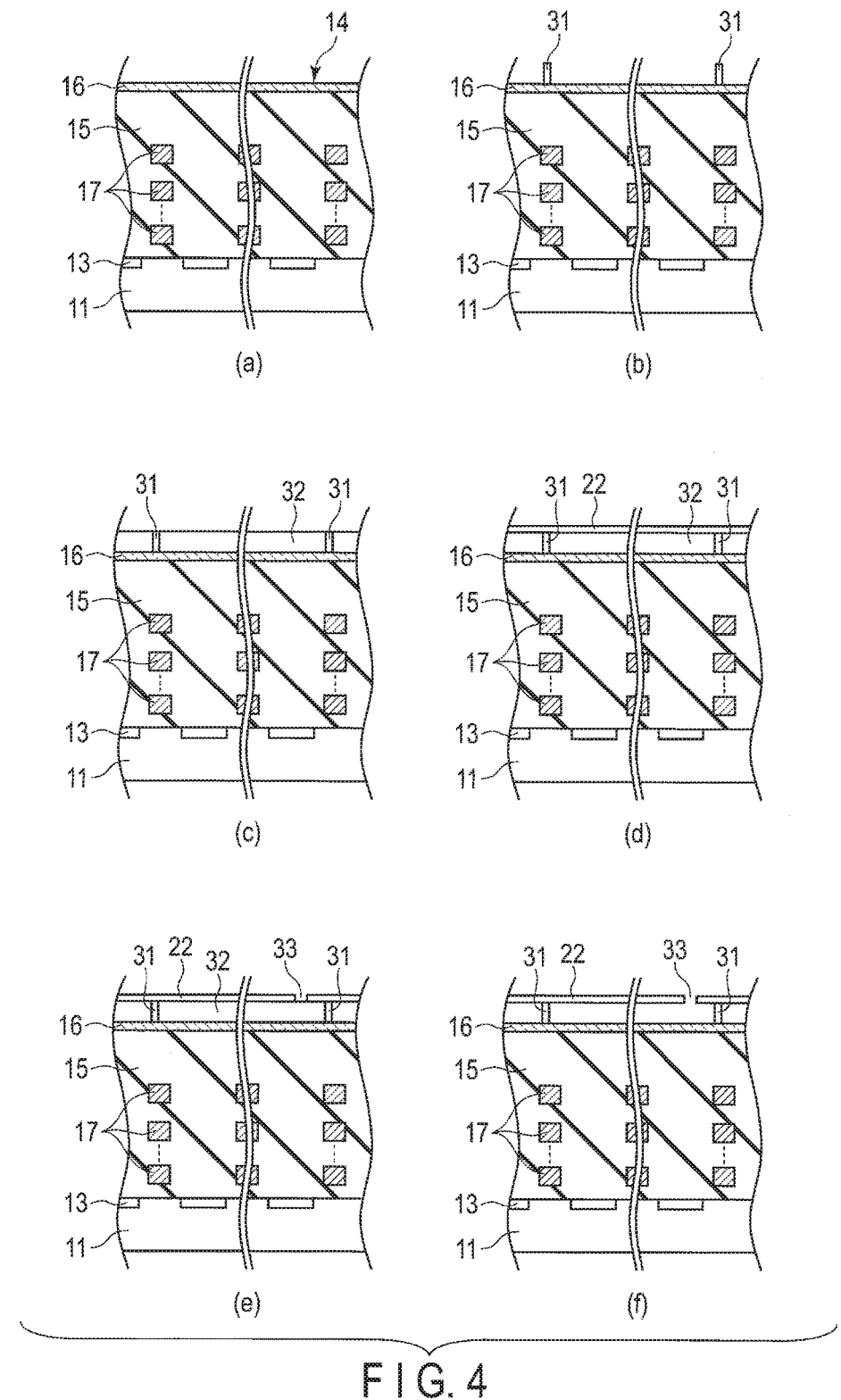
FIG. 4 is an enlarged cross-sectional view showing an example of a manufacturing process of a low-refractive-index layer of the second embodiment.

If the sensor surface 14, supporting member 31 and bottom 21 are formed integrally, the low-refractive-index layer 30 may be formed, for example, a process as shown in FIG. 4.

FIG. 4 shows a cross-sectional view of the semiconductor sensor chip 10. Using the method explained above, the substrate 11, sensing parts 13, $SiO_2$ film 15, interconnections 17, vias 18 and silicon nitride film 16 are formed initially, and the sensor surface 14 is formed (FIG. 4(*a*)). Thereupon, a material of the supporting members 31 is deposited and flattened. Then, the regions to be formed the supporting members 31 thereon are masked and the material is etched to form the supporting members 31 (FIG. 4(*b*)). A thermal oxide film may be formed thereon. A sacrifice layer 32 is deposited to the etched regions excluding the supporting members 31 and is flattened (FIG. 4(*c*)). Then, a layer which is used as the bottom 21 is deposited (FIG. 4(*d*)), and a hole 33 is opened in the layer to etch the sacrifice layer 32 (FIG. 4(*e*)). Lastly, the sacrifice layer 32 is etched (FIG. 4(*f*)).

The number of supporting members 13 may be arbitrarily determined such that a desired low-refractive-index layer 30 can be formed and maintained between the sensor surface 14 and the bottom 21 and optical data of a sample can be detected properly.

In some embodiments, the low-refractive-index layer may be formed such that a cylindrical supporting member axis of which is orthogonal to the sensor surface surrounds the periphery thereof (this is not shown). In that case, the sensor surface 14 and the bottom 21 are fixed by the cylindrical supporting member facing each other with a gap therebetween. In that case, the supporting members 13 may be omitted. Such a cylindrical supporting member may be formed separately from the bottom and of the same material used for the supporting members 13, or may be formed integrally with the semiconductor sensor chip, or may be formed integrally with the sample container. If the cylindrical supporting member may be formed integrally with the semiconductor sensor chip, the semiconductor sensor chip is formed and then the supporting member is formed on the sensor surface through a semiconductor process or injection molding. If the cylindrical supporting member is formed integrally with the sample container, the supporting member may be, for example, formed as a part of the wall extended downward below the bottom to correspond to the height of the desired low-refractive-index layer, or formed to extend downward from the lower surface of the bottom through injection molding.

In some embodiments, the sample container 20 may be a petridish including two plates with a gap therebetween as its bottom. The two plates are fixed with a gap therebetween by any of the above-described methods. The gap between the two plates may be used as a low-refractive-index layer. Such a petridish is fixed on the sensor surface such that the upper plate thereof and the sensor surface are facing each other. The bottom surface of the petridish may be adhered to the sensor surface, or may be fixed to the sensor surface with a gap therebetween such that optical data can be acquired with desired accuracy. Furthermore, the bottom of the petridish may include two or more plates such that optical data can be acquired with desired accuracy.

In such an optical sensor, a semiconductor sensor chip and a sample container may be detachably attached thereto. In that case, the supporting member may be provided in the semiconductor sensor chip side or in the sample container side.

A distance from the sensor surface 14 to the bottom 21 is given D (cf. FIG. 3(B)). If D increases, accuracy of two-dimensional positional data detected by the sensing part may decrease. This is because light from the target incident into the bottom not perpendicularly tends to go apart from its original two-dimensional position with distance. Thus, if D becomes greater, a possibility of acquiring optical data which do not correspond to the positional data will become high.

D may be defined as, for example, $0 < D \leq 100$ μm. D is preferably, for example, 10 μm or less. In that case, the positional data acquired by the semiconductor sensor chip 10 may become more accurate. If image data are acquired, the resolution thereof will become higher.

Now, a process of detecting optical data by any one of the optical sensors described above will be explained with reference to FIG. 5(A) and FIG. 5(B).

Figure 5:
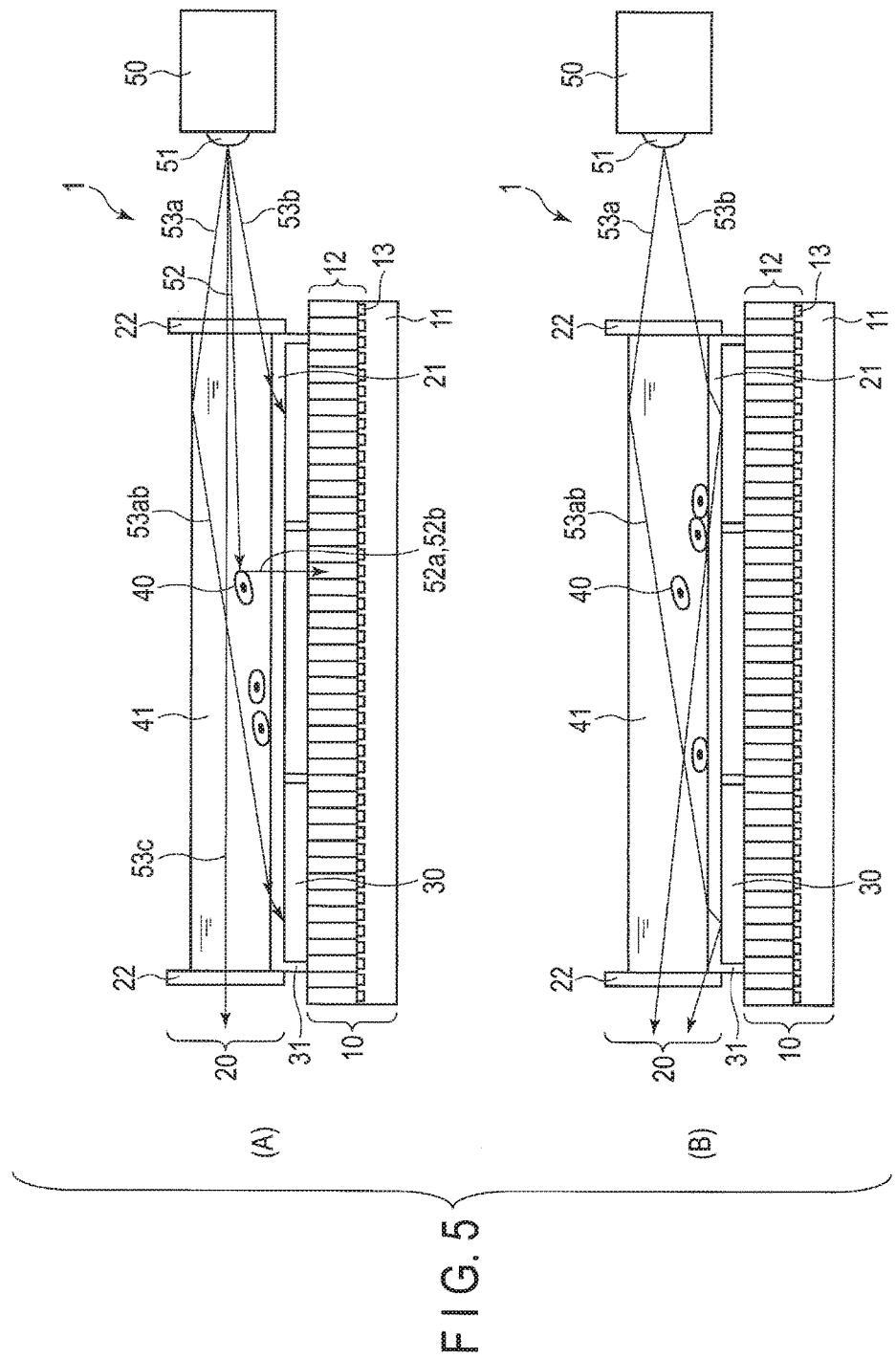
FIG. 5 is a cross-sectional view of an example of an optical sensor of an embodiment during its operation.

In FIG. 5(A) and FIG. 5(B), an example of an optical sensor including a low-refractive-index layer is shown. As in FIG. 5(A), the optical sensor 1 includes the sample container 20 in which a sample is contained during analysis. In FIG. 5(A) and FIG. 5(B), the optical sensor 1 including the sample container 20 containing a cell keeping solution 41 with cells 40 therein as a sample is depicted. In that case, the target is cells 40. During the analysis, light is emitted from the light source 51 to the sample container 20. The light may be irradiated externally to pass through the wall 22 and to enter the sample container 20.

The light enters the sample container 20, and partly, light 52 impinges on the cells and it may scatter. In the scattered light 52, light scattered sideways will be referred to as sideways scattered light. If the cells 40 contain fluorescent pigment, and the light from the light source 51 is excitation light of the fluorescence pigment, fluorescence is produced from the cells 40 by the light 52. In the sideways scattered light and fluorescence, those travels toward the bottom are referred to as sideways scattered light 52a and fluorescence 52b, and they pass the bottom, reach the semiconductor sensor chip 10, and are detected by the sensing parts 13 in their travelling direction. Therefore, a two-dimensional position where the sideways scattered light 52a or fluorescence 52b is produced can be reflected on two-dimensional positional data of the sensing parts 13. Through the above, the optical data detected by the sensing parts 13 can be associated with the positional data.

On the other hand, the light which does not hit the cells will be incident on the surface of the cell keeping solution 41 (as light 53a), bottom 21 (as light 53b) and the wall in the opposite side (as light 53b). Light 53a incident on the surface of the cell keeping solution 41 may be reflected to enter the bottom 21. Such light 53ab and light 53b incident on the bottom 21 then travel below the bottom 21 to reach the sensing parts 13 and are detected in some cases. Light 53a and light 53b are hereinafter referred to as scattered light. The scattered light is, in a detection process, detected as noise which is difficult to distinguish from the sideways scattered light 52a and fluorescence 52b of cells, and accuracy of analysis will be deteriorated. In consideration of this point, light 53a and light 53b are irradiated at the following angle to prevent light 53ab and light 53b from reaching the sensing parts 13 as shown in FIG. 5(B), and they can escape outside the sample container 20. The angle is set such that light 53a is totally internally reflected by the surface of the cell keeping solution 41, and light 53ab and light 53b are totally internally reflected by the lower surface of the bottom 21. The angle is, for example, greater than or equal to the greater one of a critical angle of light incident on the surface of the cell keeping solution with cells 40 therein and a critical angle of light incident on the bottom 21. If the optical sensor includes a low-refractive-index layer 30, it is disposed below the bottom 21, and if the optical sensor does not include a low-refractive-index layer 30, the sensor surface 14 is disposed below the bottom 21. By irradiating light onto a sample at such an angle, the scattered light can be removed efficiently without using an expensive detector, and accurate analysis is performable. This is achievable because of the light irradiation which is performed through a phototransmissive wall and a layer of the cell keeping solution 41 and the bottom 21 which can produce total internal reflection of light 53a, light 53ab and light 53b. The presence of such a layer is achieved by the above-structured sample container of the optical sensor 1.

With the low-refractive-index layer 30, light beams of many angles can be totally internally reflected when incident on the lower surface of the bottom 21. Therefore, as compared to a case where there is no low-refractive-index layer, the scattered light reaching the sensing part can be reduced more sufficiently.

Figure 6:
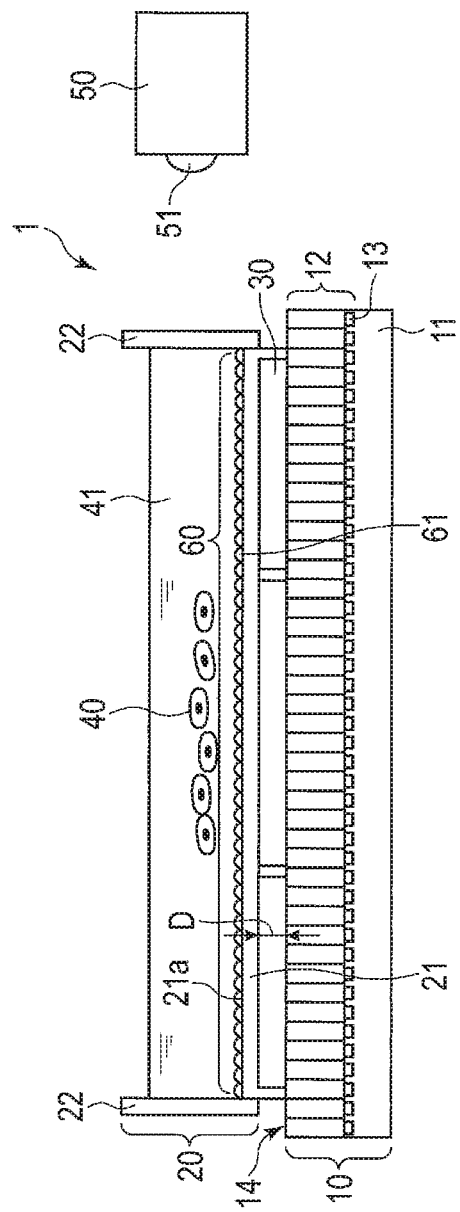
FIG. 6 is a cross-sectional view of another example of an optical sensor of an embodiment during its operation.

In some embodiments, the optical sensor 1 further may includes a lens array 60 on the upper surface 21a of the bottom 21 of the sample container as in FIG. 6. The lens array 60 includes a plurality of microconvex lenses 61 arranged in a matrix with their convex surfaces directed upward. The diameter of a microconvex lens 61 is, for example, 1 to 10 μm. The height of a microconvex lens 61 is, for example, 1 to 10 μm.

Figure 7:
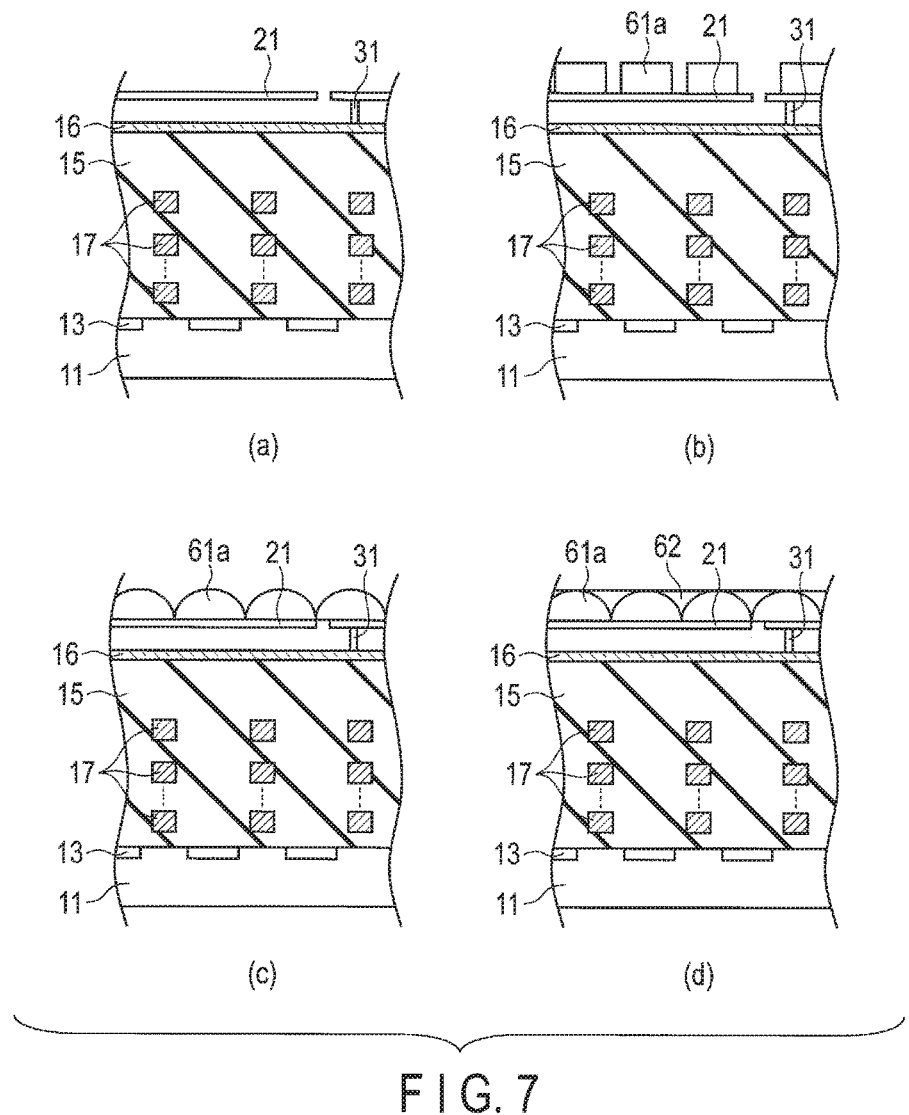
FIG. 7 is an enlarged cross-sectional view of a lens array of an embodiment during its manufacturing process.

The lens array 60 is formed on the bottom 21 through, for example, the following process shown in FIG. 7.

On the upper surface of the bottom 21 formed through the above method (FIG. 7(a)), a high-refractive-index material 61a for the microconvex lenses 61 is applied and patterned (FIG. 7(b)). Then, through a thermal deformation process, the high-refractive-index material 61a is formed into lenses, and cured by ultraviolet irradiation or heating (FIG. 7(c)). Then, a low-refractive-index material 62 is applied on the high-refractive-index material 61a and the surface thereof is flattened by, for example, spin-coating (FIG. 7(d)). The high-refractive-index material and the low-refractive-index material are formed of, for example, resins of different refractive indices each other.

As such a bottom with a lens array on its upper surface, a known microlens array may be used. Such a microlens array is available from, for example, Hamamatsu Photonics Kabushiki Kaisha and Toppan Printing Co., Ltd.

The microconvex lenses refract and gather light beams from a sample, and thus, even if a distance D between the sensor surface 14 and the bottom 21 is longer, highly accurate positional data can be acquired.

In some embodiments, the sample container 20 includes two plates with a gap therebetween as its bottom. Such sample container may be a petridish, dish or a multiwell plate with the above microlens array on the upper surface of their bottom. A region defined by the two plates and the wall is a low-refractive-index layer. With the outer bottom surface of the petridish opposed and fixed to the sensor surface, the optical sensor of an embodiment can be achieved.

Light which causes noise such as the above scattered light can be produced by, for example, a scratch or a hole in the bottom 21. Such noisy light reaches the sensing parts, and accuracy of analysis can be deteriorated. To remove the noisy light efficiently, and to improve the accuracy of analysis, the following optical sensors can be used, for example. An optical sensor which does not include a sensing part in a region on a semiconductor sensor chip where scattered light reaches; an optical sensor which includes a light blocking member which partly shields the sensor surface; an optical sensor which includes a wall with a lens, an optical sensor which includes a light blocking film which partly shields a wall, or an optical sensor which includes a filter. Such examples are detailed hereinafter.

Third Embodiment

Figure 8:
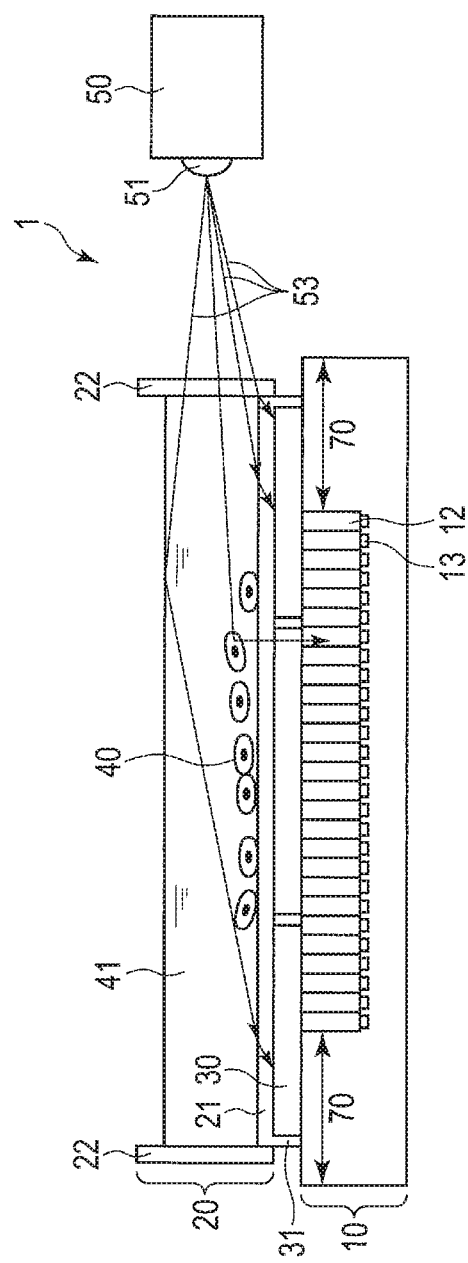
FIG. 8 is a cross-sectional view of an example of an optical sensor of a third embodiment during its operation.

FIG. 8 is a cross-sectional view of an example of an optical sensor 1 of the third embodiment, in which sensing parts 13 are excluded from a region 70 where scattered light reaches. FIG. 8 shows the optical sensor 1 including a low-refractive-index layer and a sample container 20 containing a cell keeping solution 41 with cells 40 therein as a sample. The region 70 to which scattered light reaches is a part on the semiconductor sensor chip 10, and during the using of the semiconductor sensor chip 10 of the first or second embodiment, the scattered light 53 reaches the region corresponding to the region 70. The region 70 includes, for example, a region in the proximity of the light source 51 where scattered light 53 the angle of incidence of which with respect to the bottom 21 is smaller may reach and a region distant from the light source 51 where scattered light 53 reflected by the surface of the cell keeping solution 41 and incident on the bottom 21 may reach. The position(s) of region 70 may be arranged based on an angle and a type of light from the light source 51, a type of the cell keeping solution 41, a thickness and a type of the low-refractive-index layer 30.

In some embodiments, the semiconductor sensor chip 10 does not include a sensing part 13 in a region where scattered light produced by a hole, scratch and/or supporting member reaches as in a fourth embodiment.

The above structure can prevent detection of light which should not be detected by sensing parts, that is, scattered light or the like.

Fourth Embodiment

Figure 9:
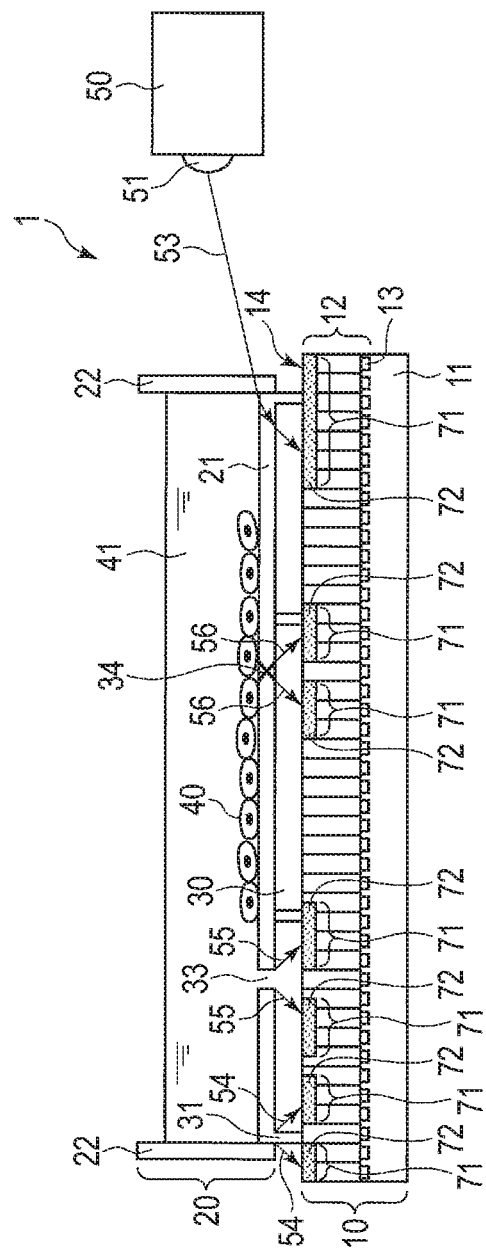
FIG. 9 is an enlarged cross-sectional view of an example of an optical sensor of a fourth embodiment during its operation.

FIG. 9 is a cross-sectional view of an example of an optical sensor of the fourth embodiment, in which a light blocking member 72 is disposed on a sensor surface 14 in a region 71 where scattered light reaches. In this example, scattered light 53 which is emitted by the light source 51 and is incident on the bottom 21 without hitting cells 40, scattered light 54 produced by a supporting member 31, scattered light 55 produced by a hole 33 in the bottom 21, and scattered light 56 produced by a scratch 34 on the bottom 21 are depicted, for example. Light 54, light 55, and light 56 produced by the supporting member 31, hole 33, and scratch 34 will reach the region 71 which includes, a region of radius 10 µm around the scratch 34, a region of radius 10 µm around the hole 33, or a region of radius 10 µm around the supporting member 31.

The light blocking member 72 is formed of, for example, a metal. The metal may be Al or Cu. The thickness of the light blocking member 72 extending perpendicularly to the sensor surface is, for example, 0.1 to 3 µm. The light blocking member 72 is formed by, for example, depositing a film of the above metal on the entirety of the sensor surface 14, removing the metal film except for the region 71 where scattered light reaches through an etching process, performing an interlayer film deposition with $SiO_2$ or the like, and planarizing the surface.

In some embodiments, the light blocking member 72 may be formed between the sensing parts 13 and the sensor surface 14. The light blocking member 72 may be formed in, for example, the phototransmissive member 15. Furthermore, a region 71 may be covered by a continuous light blocking member in a one-by-one basis, or may be covered by a plurality of light blocking members for light interception.

The above structure can prevent detection of scattered light by a semiconductor sensor chip, and optical data and corresponding positional data can be acquired accurately.

In the example of FIG. 9, the optical sensor including a low-refractive-index layer is depicted, however, the optical sensor need not include a low-refractive-index layer.

Fifth Embodiment

FIG. 10A shows a cross-sectional view of an example of an optical sensor of a fifth embodiment, in which a semiconductor sensor chip 10 includes a tapered light blocking member 72 therein. Such a tapered light blocking member 72 is arranged to be above the upper surface of sensing parts 13 and below the sensor surface 14. In the example of FIG. 10A, the optical sensor includes a low-refractive-index layer 30.

Figure 10B:
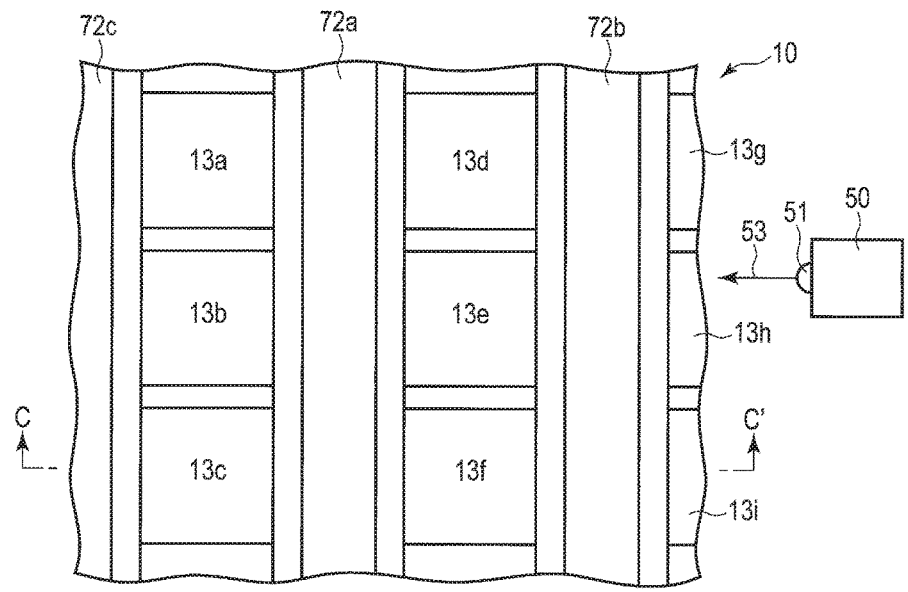
FIG. 10B is an enlarged plan view of an example of a semiconductor sensor chip of the fifth embodiment during its operation, as being viewed in an enlarged manner.

FIG. 10B is a schematic top view showing a positional relationship between the sensing parts 13 and the light blocking members 72 in section B of FIG. 10A. In the example depicted, while other elements are omitted, six adjacent sensing parts 13a to 13f and light blocking members 72a and 72b are focused for the sake of simplification. Light blocking member 72a is disposed between a line including sensing parts 13a, 13b and 13c and a line including sensing parts 13d, 13e and 13f. Light blocking member 72b is disposed between the line including sensing parts 13d, 13e and 13f and a line including sensing parts 13g, 13h and 13i. Each of light blocking members 72a and 72b are arranged such that its longitudinal direction can be orthogonal to light 53 irradiated from the light source 51. As being viewed from the top, light blocking member 72a is disposed between the line including the sensing parts 13a, 13b and 13c and the line including sensing parts 13d, 13e and 13f. In some embodiments, light blocking member 72a may be disposed directly above the sensing parts 13a, 13b and 13c, or may be disposed to partly overlap the sensing parts 13a, 13b and 13c as being viewed from the top. The same applies to light blocking members 72b and 72c. However, as being viewed from the top, at least a part of a sensing part is exposed between adjacent light blocking members. With such a structure, light from a target to be detected is incident on the sensing parts between the adjacent light blocking members and can be detected thereby. The longitudinal length of the light blocking member may be, for example, 10 μm to 10 mm, however, not being limited thereto. The length can be determined based on the size of the semiconductor sensor chip. The width of the light blocking member which is orthogonal to the longitudinal direction thereof may be, for example, 1 to 10 μm, however, not being limited thereto. A gap between the adjacent light blocking members may be, for example, 0.1 to 10 μm. The gap may be determined depending on the size of sensing parts.

Figure 10C:
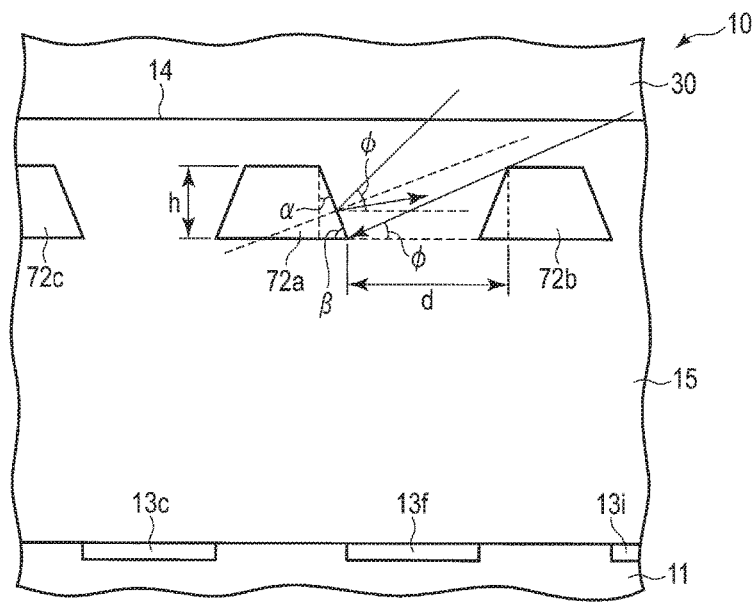
FIG. 10C is an enlarged cross-sectional view of an example of a semiconductor sensor chip of the fifth embodiment during its operation, as being viewed in an enlarged manner.

FIG. 10C is a cross-sectional view showing the sensing parts 13 and the light blocking members 72, taken along line C-C' of FIG. 10B. Light blocking members 72a and 72b each have a bottom surface and an upper surface which are parallel to the sensor surface, and have tapered side surfaces. A dihedral angle formed by the upper surface and a side surface of the light blocking member is greater than 90°. An angle α formed by a perpendicular line from an end of the upper surface to the bottom surface and a side surface is defined as 0<α<90°. Furthermore, an interior angle β of the dihedral angle formed by the bottom surface and the side surface of the light blocking member is less than 90°. Therefore, the cross-sectional view of each of light blocking members 72a and 72b, taken along line C-C' of FIG. 10B is shaped as a trapezoid upper side of which is less than the lower side. However, the cross-sectional view thereof may be a triangle bottom surface of which is parallel to the sensor surface and an apex of which is positioned in the sensor surface side. Light blocking members 72a and 72b may have the same dimensions and shape and may be apart from the sensor surface with the same gap. Light blocking members 72a and 72b can be formed through a semiconductor process.

With the tapered light blocking member 72 structured as above, detection of scattered light incident on the sensor surface 14 at a particular angle q by the sensing parts 13 can be prevented. The particular angle φ is set to be less than an angle by which light can pass between light blocking members 72a and 72b. The particular angle φ is one of any angles meeting the condition defined as φ≤tan$^{-1}$(h/d). The height of light blocking member 72a and 72b is h. D is the distance, that is A gap between the end point of the bottom surface of light blocking member 72a which is in the closest proximity to light blocking member 72b and the crossing point of the perpendicular line drawn from the end point of the upper surface of light blocking member 72b which is in the closest proximity to light blocking member 72a to the bottom surface of light blocking member 72b. If the cross-sectional view of each of light blocking members 72a and 72b is a triangle, a distance between the end point of the bottom surface of light blocking member 72a which is in the closes proximity to light blocking member 72b and the crossing point of the perpendicular line drawn from the apex of the triangular cross-section of light blocking member 72b to its bottom surface is d. Furthermore, the particular angle φ is set such that light hitting a side surface of a light blocking member cannot be reflected toward sensing parts. The particular angle φ is one of any angles meeting the condition defined as φ≤2α.

In some embodiments, the particular angle α may differ in the light blocking members 72 depending on their positions on the semiconductor sensor chip. In some embodiments, although this is not shown, the light blocking members 72 may be multilayered in the direction perpendicular to the sensor surface 14.

With the side surfaces having such an angle α, even if a plurality of separated light blocking members are used, scattered light incident on sensing parts can be reduced.

Figure 10D:
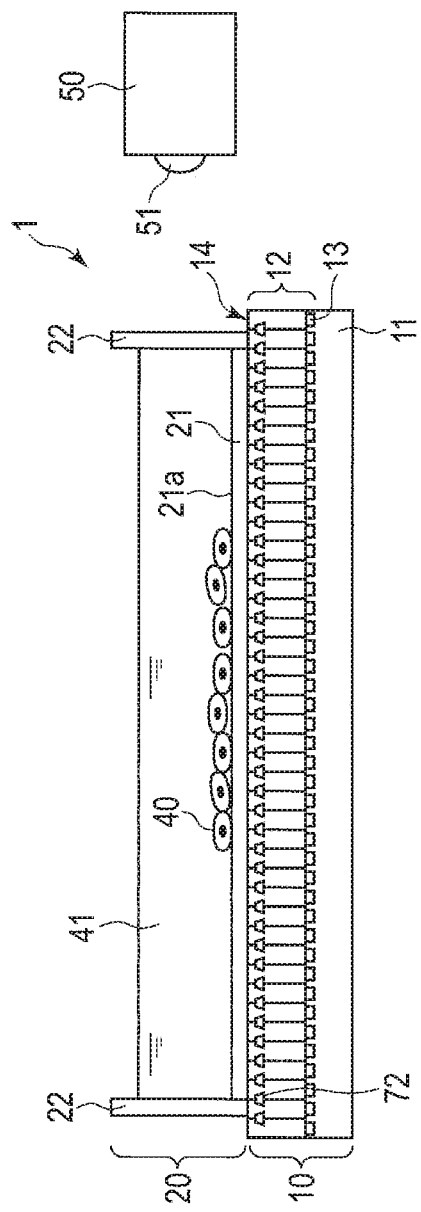
FIG. 10D is a cross-sectional view of an example of the optical sensor of the fifth embodiment.

The optical sensor structured as above need not necessarily include a low-refractive-index layer. FIG. 10D shows an example of such an optical sensor. When a low-refractive-index layer is omitted, the tapered light blocking members 72 described as above are used instead, and scattered light can be prevented from reaching sensing parts 13. Therefore, detection of a target can be performed. Such an optical sensor may be realized as the optical sensor 1 of the first embodiment including the semiconductor sensor chip 10 with the tapered light blocking members 72 as above.

In some embodiments, such a light blocking member may be replaced with an interconnection having tapered side surfaces as above.

Sixth Embodiment

Figure 11A:
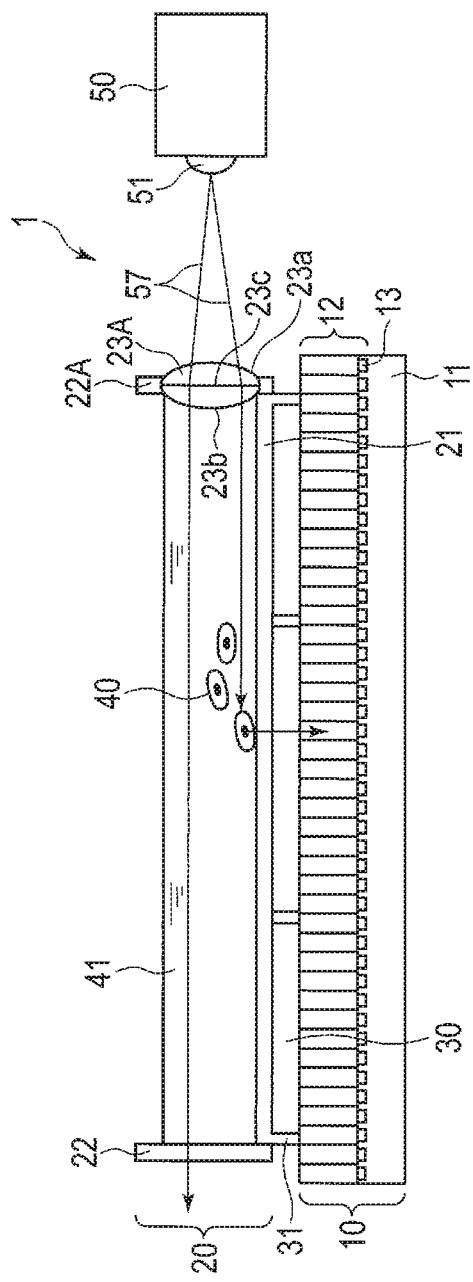
FIG. 11A is a cross-sectional view of an example of an optical sensor of a sixth embodiment during its operation.

FIG. 11A is a cross-sectional view of an example of an optical sensor 1 of the sixth embodiment, in which a wall 22A further includes a lens 23A. The optical sensor 1 may be formed the same as any of the aforementioned optical sensors except that the wall 22A includes the lens 23A.

The lens 23A may be disposed at least in a desired part on a light passage between the light source 51 and a sample including the region of the wall 22A. Light 57 emitted from the light source 51 passes through the lens 23A disposed in the desired part of the wall 22A to be converged at an angle which is substantially parallel to the bottom 21. Such a lens may be, for example, a biconvex lens, planoconvex lens, biconcave lens, planoconcave lens, prism lens or any combination thereof.

The three-dimensional shape of the lens 23A may be, for example, a disc, sphere, flat sphere, or column including a pillar and a prism. FIG. 11A shows the optical sensor 1 including the lens 23A as a circular biconvex lens. The lens 23A is disposed such that one surface 23a faces the light source 51, the other surface 23b faces the inside of the sample container 20, and the principal plane 23c is arranged orthogonal to the bottom 21. Here, the principal plane is an imaginary plane at the intersection of the path of light before entering the lens and the path of light after exiting the lens. With the lens 23A disposed as above, light from the light source 51 enters the surface 23a.

Figure 11B:
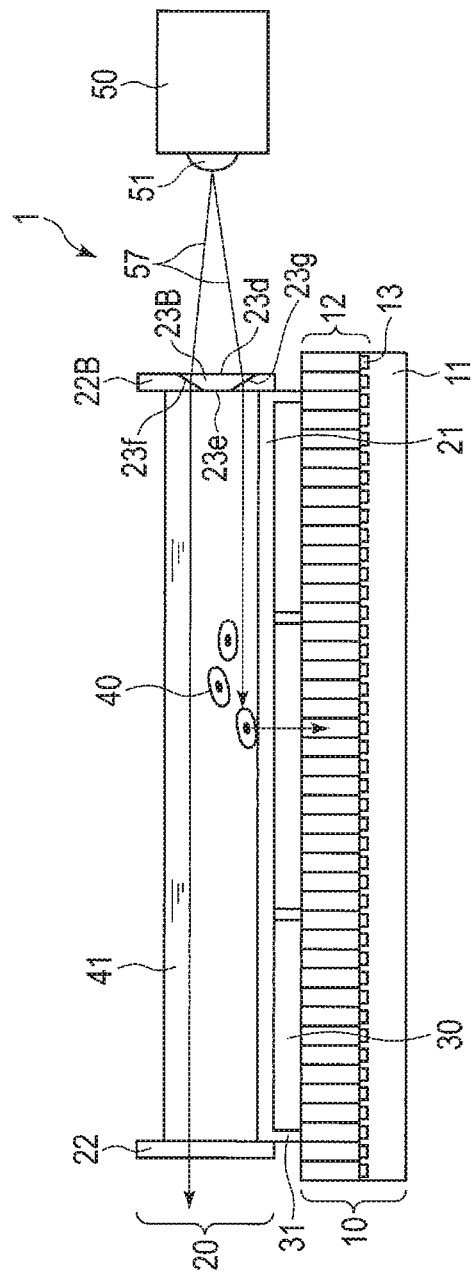
FIG. 11B is a cross-sectional view of an example of the optical sensor of the sixth embodiment during its operation.

FIG. 11B is a cross-sectional view of an optical sensor including a quadrangular prism lens the bottom surface of which is a trapezoid. The axis of the quadrangular prism lens 23B is orthogonal to light 57 and is parallel to the bottom 21. FIG. 11B shows a cross-section of the lens 23B, taken orthogonally to the axis thereof. The cross-section is a trapezoid long side 23d of which faces the light source 51 and short side 23e of which faces the inside of the sample container 20. That is, the side surface depicted as the side 23d in FIG. 11B faces the light source 51. With the lens 23B disposed as above, light 57 incident on the side surfaces of the trapezoid depicted as sides 23f and 23g connecting the long and short side of the trapezoid in FIG. 11B can be refracted into an angle substantially parallel to the bottom 21.

The direction of arrangement of the quadrangular prism lens bottom surface of which is a trapezoid is not limited to that of the example of FIG. 11B. For example, the long side 23d need not face the light source. FIG. 11C shows a cross-sectional view of an optical sensor including such a lens. A quadrangular prism lens 23C the bottom surface of which is a trapezoid of FIG. 11C is disposed such that a long side 23h of the trapezoid faces upward and a short side 23i of the trapezoid faces the semiconductor sensor chip. In that case, light 57 is irradiated from the light source 51 on the surface depicted as side 23j facing the light source. Light 57 is refracted at an angle parallel to the bottom 21 by the lens 23C. Either one of the side surfaces of lens 23C facing the light source and the inside of the sample container may be orthogonal to the bottom 21.

The lens may be disposed to occupy the entire area of the wall in the height direction. In that case, the wall may be formed such that its desired part can function as any of the above-described lenses.

The lens may be curved or bent to conform to the shape of the wall. That is, if the wall defining the sample container is a cylinder, the lens may be curved to conform to the curved periphery of the cylinder. Furthermore, if the wall is a polyangular cylinder, the lens may be bent to conform to the bending periphery of the polyangular cylinder.

To correspond to a desired region of the wall, one or more of the lens may be adjusted. If a plurality of disc lenses are disposed on a cylindrical or polyangular cylinder wall, they may be arranged in an array to cover a part of the periphery of the wall, one side surface of the wall, or a plurality of side surfaces of the wall. If a plurality of columnar lenses are disposed, they may be arranged such that their axes of are parallel to each other in the height direction of the wall.

The lens may be fixed to the outer surface of the wall of the sample container, or may be fixed to the inner surface of the wall of the sample container, or may be disposed to pass through the wall.

With the wall including the above lenses, light which fails to hit a target and is incident on the bottom to reach sensing parts can be reduced. Therefore, optical data from the target can be acquired accurately.

The optical sensor structured as above need not necessarily include a low-refractive-index layer. If the low-refractive-index layer is omitted, the above lens can instead prevent scattered light reaching sensing parts. Therefore, detection of a target can be performed. Such an optical sensor may be realized as the optical sensor 1 of the fifth embodiment including a wall with any of the above lenses. In that case, the optical sensor does not need to include a light blocking member of the fifth embodiment.

Seventh Embodiment

Figure 12:
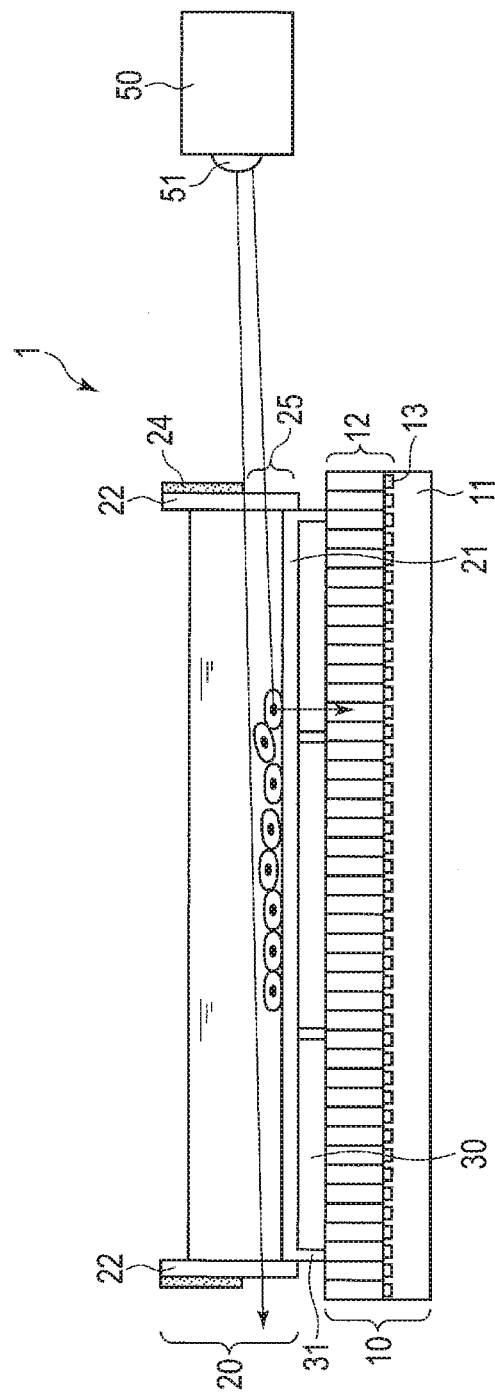
FIG. 12 is a cross-sectional view of an example of an optical sensor of a seventh embodiment during its operation.

FIG. 12 is a cross-sectional view of an example of an optical sensor of the seventh embodiment. FIG. 12 shows an optical sensor 1 including a wall 22 side surface of which is partly covered with a light blocking film 24. In the example of FIG. 12, the optical sensor includes a low-refractive-index layer 30. Furthermore, the optical sensor 1 includes a sample container which contains a cell keeping solution 41 with cells 40 therein. The light blocking film 24 is, for example, a publically-known film which can shield visible light, ultraviolet light, and infrared light emitted from the light source 51 of the illumination unit 50. In the present embodiment, a region 25 of the wall 22 which is not covered by the light blocking film 24 is determined based on the quantity of light irradiated thereon, type of light, and/or a gap between the light source and the wall. The region may be shaped as a band parallel to the bottom, circle, polygon, or spot. The light blocking film 24 is disposed to cover at least the wall on the light passage from the light source to the sample, or may be disposed to cover the entirety of the side surface of the outer surface of the wall 22. The light blocking film 24 may cover the outer surface or the inner surface of the wall 22, or may cover a region of the outer surface and the corresponding region of the inner surface.

When the light source 51 of the illumination unit 50 becomes farther from the wall 22, the angle of incidence of the light on the bottom 21 becomes greater, and thus, scattered light reaching sensing parts can be decreased. A suitable gap between the light source 51 and the wall 22 may change depending on the shape and size of the region 25. Therefore, a gap between the light source 51 and the wall 22 and the shape and size of the region 25 is preferably determined based on desired accuracy of optical data and corresponding positional data.

With the light blocking film structured as above and light irradiated from a certain distant point of the wall, light which fails to hit a target and is incident on the bottom to reach sensing parts can be reduced. Therefore, optical data from the target can be acquired accurately.

The optical sensor structured as above need not necessarily include a low-refractive-index layer. If the low-refractive-index layer is omitted, the above light blocking film can instead prevent scattered light reaching sensing parts. Therefore, detection of a target can be performed. Such an optical sensor may be realized as the optical sensor 1 of the fifth embodiment including the wall with the light blocking film. In that case, the optical sensor does not need to include a light blocking member of the fifth embodiment.

Eighth Embodiment

Figure 13:
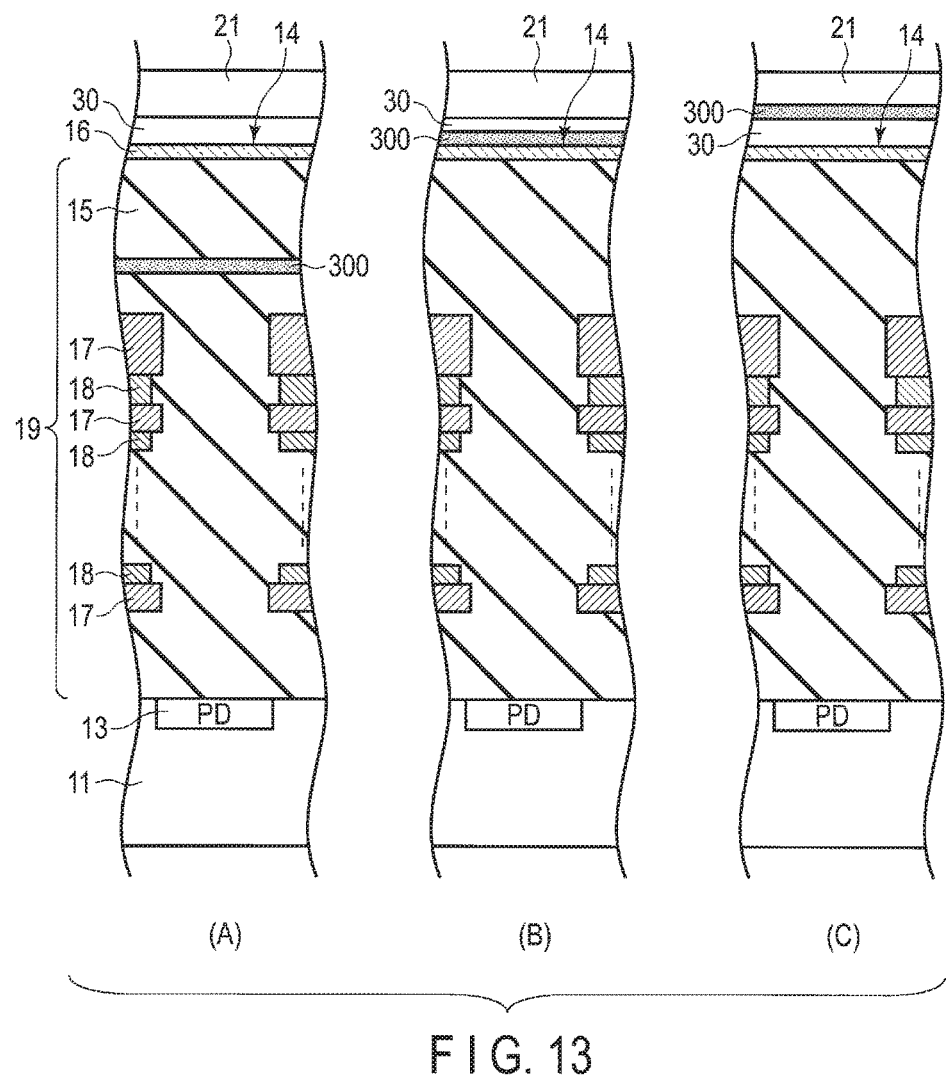
FIG. 13 is an enlarged cross-sectional view showing an example of a position of a filter included in an optical sensor of an eighth embodiment, as being viewed in an enlarged manner.

FIG. 13(A), FIG. 13(B), and FIG. 13(C) are cross-sectional views of an optical sensor including a filter 300 between sensing parts 13 and a bottom 21, in which the bottom 21 and the semiconductor sensor chip 10 are shown in an enlarged manner. In the examples of FIG. 13(A), FIG. 13(B), and FIG. 13(C), the optical sensor 1 includes a low-refractive-index layer 30.

The filter 300 of the optical sensor may be formed between the sensing parts 13 and the sensor surface 14 as shown in FIG. 13(A). Or, the filter 300 may be formed in the uppermost part of the semiconductor sensor chip as shown in FIG. 13(B). Or, the filter 300 may be formed below the bottom 21 as shown in FIG. 13(C). The filter 300 may be formed through a semiconductor process. Or, the filter 300 as in FIG. 13(B) may be formed as the uppermost surface of the semiconductor sensor chip. Or, the filter 300 as in FIG. 13(C) may be formed to be adhered to the lower surface of the bottom 21.

The filter 300 is formed to pass and absorb particular wavelengths. That is, for example, the filter 300 absorbs excitation light and passes fluorescence. In that case, fluorescence from a target including a fluorescence pigment can be detected efficiently.

The filter 300 may be, for example, an inorganic filter and/or an organic filter. The inorganic filter may be, for example, a multilayered filter or a plasmonic filter. The multilayered filter includes low refraction layers and high refraction layers deposited alternately. If, for example, silicon oxide is used as a low refraction material, and zirconium oxide is used as a high refraction material, the thickness of the silicon oxide layer is preferably 62±5 nm, and the thickness of the zirconium oxide layer is preferably 38±5 nm. Such a multilayered film can properly reflect light of 360±30 nm wavelength with respect to light of 510 nm wavelength. Specifically, an inorganic filter including a pair of the above two types of oxide layers stacked thirty times can obtain a rejection ratio of 1/100000. The organic filter can be formed of a pigment or a dyestuff.

With the filter structured as above, light which fails to hit a target and reaches sensing parts can be reduced. Therefore, optical data from the target can be acquired accurately.

In some embodiments, a single semiconductor sensor chip may include two or more types of filters. Thereby, lights of different wavelengths can be analyzed at the same time.

The optical sensor structured as above need not necessarily include a low-refractive-index layer. If the low-refractive-index layer is omitted, the above filter can instead prevent scattered light reaching sensing parts. Therefore, detection of a target can be performed. Such an optical sensor may be realized as the optical sensor 1 of the fifth embodiment can include the filter. In that case, the optical sensor does not need to include a light blocking member of the fifth embodiment.

If a low-refractive-index layer is omitted from an optical sensor, elements used to prevent light from reaching sensing parts of the fifth to eighth embodiments may be used in combination in the optical sensor. For example, an optical sensor may include a light blocking member of the fifth embodiment in the semiconductor sensor chip and a lens of the sixth embodiment in the wall. Alternatively, an optical sensor may include a light blocking member of the fifth embodiment in the semiconductor sensor chip and a light blocking film of the seventh embodiment in the wall. Alternatively, an optical sensor may include a lens of the sixth embodiment and a light blocking member of the fifth embodiment in the wall. Such optical sensors may further include a filter of the eighth embodiment. Such optical sensors may further include a semiconductor sensor chip of the first embodiment and/or a light blocking member of the third embodiment.

Ninth Embodiment

FIG. 14(A) and FIG. 14(B) show an example of an optical sensor of the ninth embodiment. The optical sensor includes channels. FIG. 14(A) shows the optical sensor 1 including channels 90. In the example of FIG. 14(A), the optical sensor 1 includes a low-refractive-index layer. The optical sensor need not necessarily include a low-refractive-index layer. FIG. 14(B) is a cross-sectional view of the optical sensor 1, taken along line B-B' of FIG. 14(A). As in FIG. 14(A) and FIG. 14(B), the optical sensor 1 includes channels 90 inside the bottom 21. In the bottom 21, the channels 90 may be disposed to be below the upper surface 21a and above the lower surface 21b. The channel 90 may be formed as a circular cylinder or a prism cross-section of which is a polygon. As in FIG. 14(A), the channels 90 may be arranged parallel to one another such that their long axes are parallel to the bottom 21. However, the arrangement of the channels 90 is not limited thereto. For example, additional channels (not shown) which are orthogonal to the channels 90 may be arranged such that channels in a lattice pattern can be achieved.

FIG. 14(C) shows part C of FIG. 14(B) in an enlarged manner, and therein, the inside of the channel 90 communicates with the inside of the sample container 20 via an aperture 91. In some embodiments, the aperture 91 may be opened/closed by a lid 93. The opening/closing operation is performed by, for example, an electromagnetic switch such as a mechanical electrical microswitch (MEMS). FIG. 14(C) schematically shows an example of the aperture 91 which is opened by such a switch. FIG. 14(D) schematically shows an example of the aperture 91 which is closed by such a switch. The aperture 91 with an electromagnetic switch includes, for example, an electrode 92a disposed in the proximity of the aperture 91, a lid 93 with an electrode 92b at the aperture side, and a plurality of springs 94 which connect the lid 93 to the wall of the channel 90. Thereby, the switch functions such that electrode 92b of the lid 93 is pulled to the aperture 91 when a voltage is applied to electrode 92a, and the aperture 91 is blocked. When no voltage is applied to electrode 92a, the lid 93 is pulled off the aperture 91 by the springs, and the aperture 91 is opened.

With the channel 90 structured as above, a desired chemical agent can be delivered to a sample in a particular position on the two-dimensional region of the sample container 20, or a sample in a particular position on the two-dimensional region can be collected. The chemical agent can, for example, change characteristics of a target or destruct the target. If the target is cells, change of characteristics includes, for example, changing color of the cells, quantity of expression of genes in the cells, or inactivation of the cells or a substance in the cells. Such a chemical agent is any one of publically-known chemical agents.

The optical sensor including channels may further include chambers in some embodiments. As in FIG. 15(A), chambers 95 are disposed above the channels 90 in the bottom 21. FIG. 15(B) shows part B of FIG. 15(A) in an enlarged manner. In the example of FIG. 15, the optical sensor includes a sample container containing a cell keeping solution 41 with cells therein as a sample. In the bottom 21, the chambers 95 are disposed below the upper surface 21a and above the channels 90. The chamber 95 is, for example, a hollow rectangular parallelepiped, or a hollow sphere. The chambers 95 are arranged in a matrix including rows and columns of desired numbers. The position of the chambers 95 may be set to correspond to the position of cells 40 (not shown). That is, the chambers 95 are disposed below cells 40 such that one chamber 95 matches one cell 40. In this example, a channel 90 includes an aperture 91 which connects the inside of the channel 90 to the inside of the chamber 95. The aperture 91 may be structured the same as the above aperture. Opening/closing of the aperture 91 may be performed through the same mechanism as above. The chamber 95 includes a through-hole 96 by which the inside of the chamber 95 communicates with the inside of the sample container 20.

With the chambers 95 and the channels 90 structured as above, a treatment of a sample in a particular position on the two-dimensional region of the sample container 20 can be performed. The treatment includes, for example, heating, destruction, or polymerase chain reaction (PCR) of the sample. Heating can be performed by, for example, chambers including nanowires therein. Destruction can be performed through, for example, electroporation by chambers including electrodes therein. The destructed sample can be collected by the channels. The PCR can be performed by the chambers if the sample is a biological sample. In that case, for example, an agent required for the reaction is delivered by the channels, and at the same time or before/after the delivery, nucleic acid can be collected inside the chambers from the sample thereabove. The collected nucleic acid is managed under a controlled temperature. Obtained products are collected by the channels.

The optical sensor with the channels or with the channels and the chambers need not necessarily include a low-refractive-index layer. Instead of a low-refractive-index layer, such an optical sensor may include any combination of the elements used to prevent scattered light from reaching sensing parts in the fifth to eighth embodiments.

In some embodiments, in the above optical sensor including channels or channels and chambers but not including a low-refractive-index layer, a wall can be detachably attached. In such an optical sensor, the bottom may function as a sample-supporting plate on which a sample is arranged. The sample to be analyzed in such an optical sensor includes, for example, a viscous sample, liquefied sample of a little quantity or a solid sample. Such an optical sensor may include, instead of a low-refractive-index layer, a light blocking member of the fifth embodiment and/or a filter of the eighth embodiment to prevent scattered light from reaching sensing parts.

Furthermore, based on the above, additional embodiments can be presented as follows.

Tenth Embodiment

Figure 16:
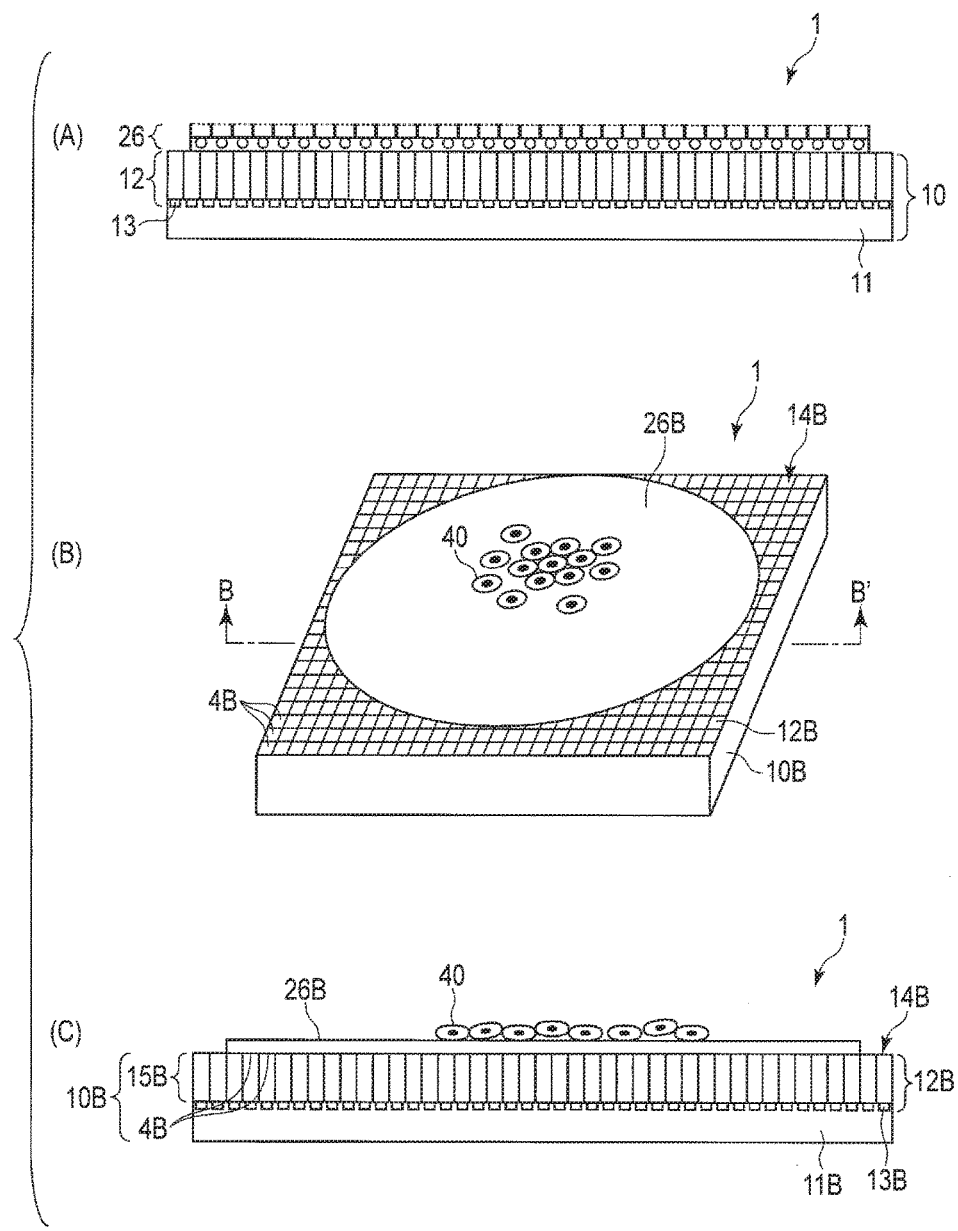
FIG. 16 is a cross-sectional view showing an example of an optical sensor of a tenth embodiment.

FIG. 16(A) is a cross-sectional view of an example of an optical sensor of the tenth embodiment. The optical sensor 1 includes a semiconductor sensor chip 10 and a phototransmissive sample-supporting plate 26. The semiconductor sensor chip 10 includes a substrate 11 and a plurality of sensing parts 13. The sensing parts 13 are arranged to face upward in a matrix on the two-dimensional region on one main surface of the substrate 11 in order to provide a sensor surface 14 corresponding to the two-dimensional region. The semiconductor sensor chip 10 may optionally include a light blocking member of the fifth embodiment and/or a filter of the eighth embodiment. The sample-supporting plate 26 is positioned above the sensor surface 14 to be opposed to the sensing parts 13, and includes channels 90 and chambers 95 inside thereof. The channels 90 and the chambers 95 may be structured as in the ninth embodiment. The chambers are positioned above the channels. The chambers and the channels may communicate with each other through apertures which can be opened/closed. Furthermore, the chambers and the upper part of the sample-supporting plate may communicate through additional apertures. The sample-supporting plate 26 may be formed with the same dimension, shape, and material as those of any of the above-described bottoms.

The optical sensor 1 need not include chambers. In that case, the channels and the upper part of the sample-supporting plate communicate with each other through apertures.

Such an optical sensor 1 may be interpreted as the optical sensor of the ninth embodiment including channels or channels and chambers, wall of which is removed.

Such an optical sensor 1 may include a low-refractive-index layer of an above-described embodiment between the sensor surface of the semiconductor sensor chip and the bottom of the sample-supporting plate.

With the optical sensor structured as above, detection of light which does not impinge on a target and passes through the bottom can be prevented, and an additional test of the target observed by the optical sensor can be performed simply.

Furthermore, based on the above embodiment, an additional embodiment can be achieved as follows. FIG. 16(B) and FIG. 16(C) show an example of the additional embodiment. FIG. 16(B) is a perspective view of the optical sensor 1 of the additional embodiment, and FIG. 16(C) is a cross-sectional view of the optical sensor 1, taken along line B-B' of FIG. 16(B).

The optical sensor 1 is structured as that of FIG. 16(A) except that channels 90 and chambers 95 are omitted. That is, the optical sensor 1 includes a semiconductor sensor chip 10*b* and a phototransmissive sample-supporting plate 26B. The semiconductor sensor chip 10B includes a substrate 11B and a plurality of sensing parts 13B. The sensing parts 13B are arranged to face upward on the two-dimensional region on one main surface of the substrate 11 in a matrix, and they form a sensor surface 14B corresponding to the two-dimensional region. The semiconductor sensor chip 10B may include a light blocking member of the fifth embodiment and/or a filter of the eighth embodiment. The sample-supporting plate 26B is positioned above the sensor surface 14B to be opposed to the sensing parts 13B.

In such an optical sensor 1, the sensing parts 13B each sense light from the sample substantially directly above thereof, and in this case, the light is irradiated on the sample such that its angle of incidence on the upper surface of the sample-supporting plate 26B can be a critical angle or more.

With the optical sensor structured as above, detection of light which does not impinge on a target and passes through the bottom can be prevented.

Eleventh Embodiment

In the eleventh embodiment, a light source may be fixed to a semiconductor sensor chip of an embodiment.

Figure 17A:
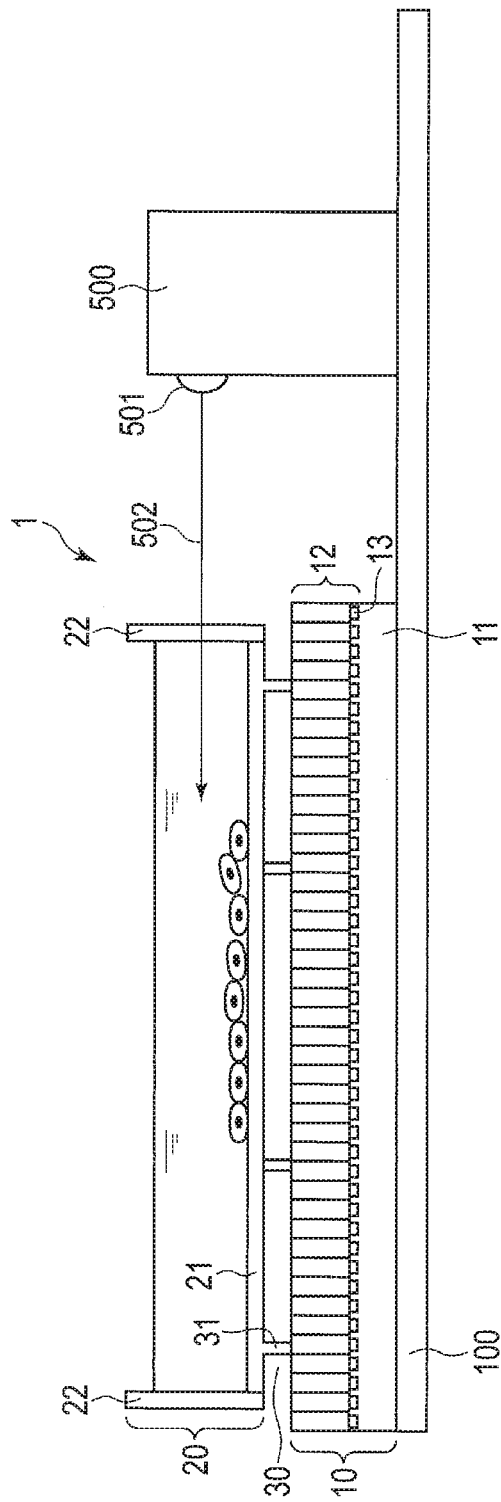
FIG. 17A is a cross-sectional view showing an example of an optical sensor of an eleventh embodiment.

An optical sensor with a fixed light source is structured as follows as in FIG. 17A. The optical sensor 1 includes a supporting board 100 and a light source 501 fixed to the supporting board 100. The light source 501 is, for example, disposed in an illumination unit 500 as in FIG. 17A. The supporting board 100 may be fixed to the lower surface of the substrate of the semiconductor sensor tip 10. The light source 501 may be fixed to face the semiconductor sensor chip 10. The supporting board 100 may be phototransmissive. The supporting board 100 may be formed of $SiO_2$ or glass epoxy. The thickness of the supporting board 100 can be, for example, 100 µm to 2 mm. The supporting board 100 is adhered to the semiconductor sensor chip 10 and the illumination unit 500 by, for example, an adhesive agent.

Figure 17B:
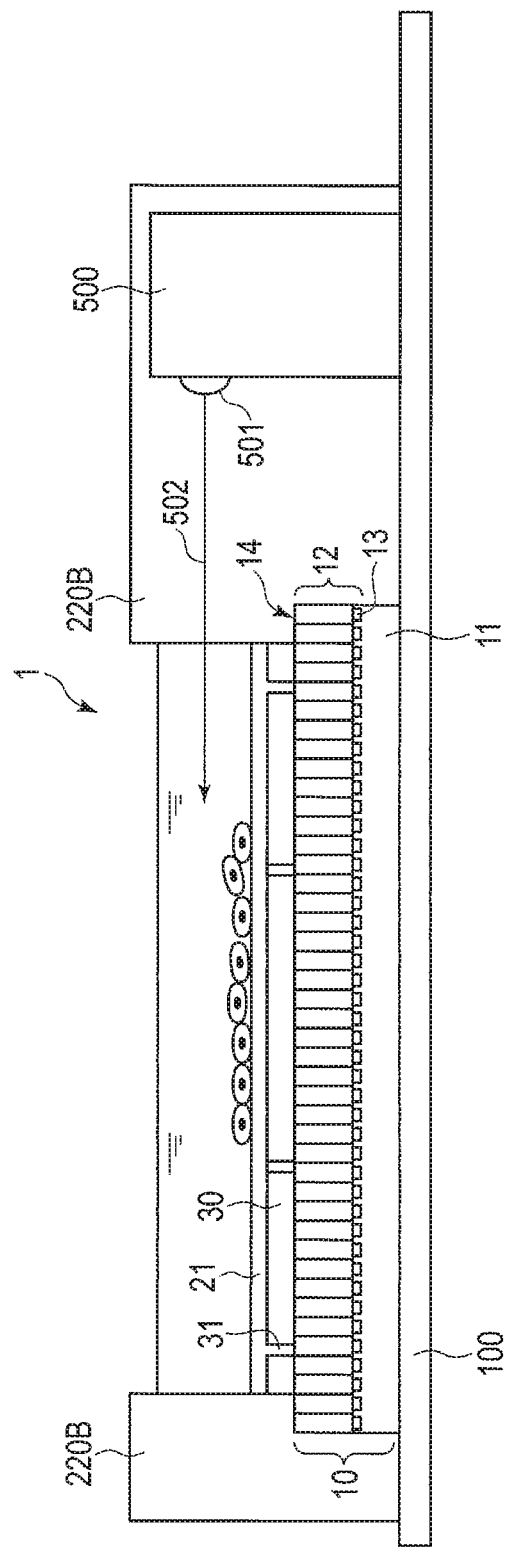
FIG. 17B is a cross-sectional view showing another example of the optical sensor of the eleventh embodiment.

In some embodiments, the light source 501 may be disposed inside the wall 220B as in FIG. 17B. In that case, the wall 220B extends in its thickness direction outward the sample container parallel to the bottom 21. The light source 501 is disposed within the thickness of the wall 220B. The thickness of the wall 220B is determined optionally. The light source 501 and the illumination unit 500 may be embedded in the wall 220B, and in that case, the part inside the wall 220B except for the light source 501 and the illumination unit 500 is filled with the material of the wall 220B. The wall 220B may extend from the upper surface of the supporting plate 100 and/or the sensor surface 14. The wall 220B is formed of, for example, a resin. Since the light source 510 is disposed inside the wall 220B, the area of the light source 501 exposed to air can be reduced and scattered light can be reduced.

In some embodiments, the wall 220B may be structured to converge light 502 entering the sample container 20 to an angle which is substantially parallel to the bottom 21. For example, a material which partly changes a traveling direction of light 502 may be disposed on the light passage inside the wall 220B. Alternatively, the shape of at least a part of the region of the wall 220B on the light passage may be formed such that the wall 220B can function as above. Such a light converging material can be, for example, a lens of the sixth embodiment or a light blocking film of the seventh embodiment. To form the wall 220B to converge light, the region on the light passage in the wall facing the inside of the sample container 20 may be formed to function as a lens of the sixth embodiment, for example.

Figure 17C:
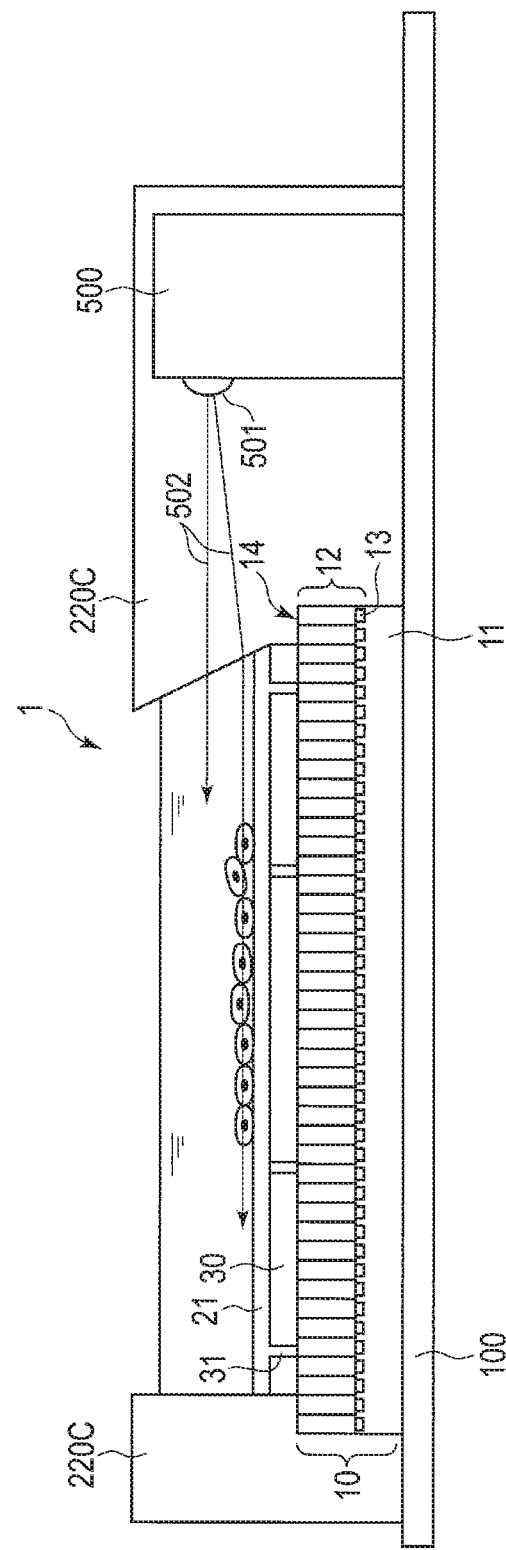
FIG. 17C is a cross-sectional view showing another example of the optical sensor of the eleventh embodiment.

In some embodiments, the optical sensor 1 includes a wall 220C surface of which faces the inside of the sample container 20 in the region on the passage of light 502 is tilted at an angle less than 90° with respect to the bottom 21. FIG. 17C shows a cross-sectional view of such an optical sensor. Such a wall 220C can be interpreted to function as the lens 23 of the sixth embodiment as in FIG. 11C. Since the wall 220C is partly tilted as above, light 502 can be refracted to be substantially parallel to the bottom 21.

Analyzer

According to an embodiment, an analyzer including an optical sensor structured as above can be provided. Hereinafter, the analyzer will be explained with reference to FIG. 18.

As in FIG. 18(A), the analyzer is configured to perform analysis of a target, and includes any of aforementioned optical sensors, illumination unit including any of aforementioned light sources, manipulator, semiconductor sensor chip of the optical sensor, and controller electrically connected to the manipulator. The electrical connection can be achieved either with a wire or wirelessly. The optical sensor acquires optical data associated with two-dimensional positional data of the target and sends the optical data to the controller as an electrical signal. The optical data associated with the positional data may be acquired as an image. The controller determines a region to be processed by the manipulator on the basis of the optical data acquired by the semiconductor sensor chip, positional data associated with the optical data, and threshold condition predetermined based on the optical and positional data and operates the manipulator. The controller may include a processing device, storage device, input device, image processing device, output device, radio transmitter/receiver. The controller is, for example, a computer. The determination of a region to be processed by the manipulator may be performed either automatically or manually on the basis of data output to the output device.

The manipulator is a unit configured to perform a particular process to a target in a particular position. The particular process includes, for example, collection, heating, destruction, deactivation of the target and/or application of a chemical agent. The manipulator may include a manipulation tool used to perform the above process. The manipulation tool is, for example, tweezers, laser, microsyringe and/or microneedle. The analyzer may include aforementioned channels and chambers as such a manipulator. The manipulator may further include a mechanism (operation mechanism) to operate a manipulation tool in accordance with an instruction of the controller.

In some embodiments, the controller may further be electrically connected to the illumination unit as shown in FIG. 18(B). In that case, the controller can switch an on/off state of the light source to control light. In some embodiments, the controller determines quantity of light and/or type of light to be irradiated onto the optical sensor on the basis of the data acquired by the semiconductor sensor chip and adjusts the quantity of light and/or type of light from the illumination unit. The determination of quantity of light and/or type of light may be performed either automatically or manually on the basis of data output to the output device.

Figure 19:
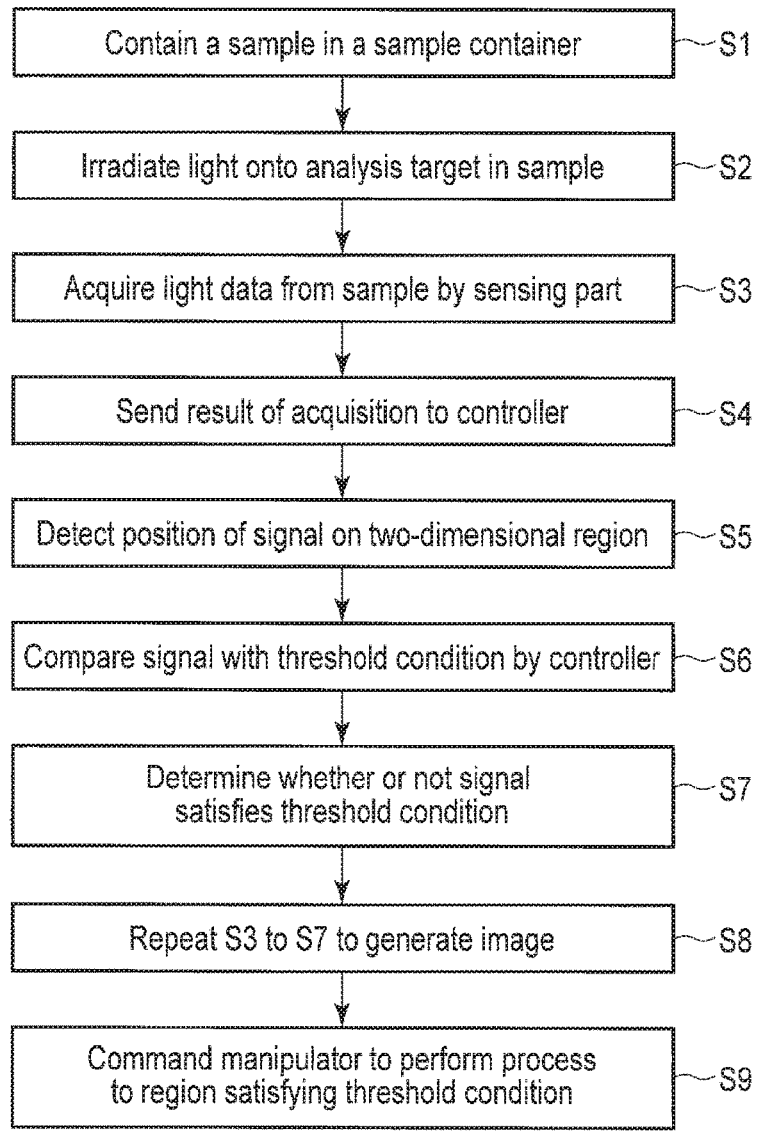
FIG. 19 is a flowchart showing an example of a procedure of analysis by the analyzer of an embodiment.

The analyzer can be used through steps shown in FIG. 19.

Initially, a sample including a target is contained in the sample container (S1). If the target is cells, they may be incubated in an incubator with their condition maintained. Then, light is irradiated toward the sample container in a darkroom such that the light impinges on the target (S2). Then, the sensing part acquires optical data of the sample under the control of the controller based on a program preliminarily stored (S3). Under the control of the controller, the sensing part converts the acquired data into an electric signal and sends the signal to the controller (S4). Upon receipt of the signal, the controller detects a position of the sensing part which has acquired the electric signal in the two-dimensional region (S5). Step S5 may be performed concurrently with step S3. In that case, the optical data and the positional data are together sent to the controller. The controller compares the received electric signal with a predetermined threshold condition (S6). Then, the controller determines whether or not the electric signal satisfies the threshold condition on the basis of a result of comparison (S7). The controller repeats a process loop including steps S3 to S7 to produce an image (S8). Using the results of S7, the manipulator, under the control of the controller, performs a process corresponding to the threshold condition to a region corresponding to positions of the sensing part satisfying the threshold condition (S9).

With the analyzer structured as above, analysis of optical data from a target and/or process of a target on the basis of a result of the analysis can be performed more simply.

In some embodiments, the analyzer may not include a wall or a bottom of the sample container. In that case, a sample is disposed on the semiconductor sensor chip and light from a light source is directly irradiated onto the sample during the analysis. With the analyzer structured as above, analysis of optical data from a target and/or process of a target on the basis of a result of the analysis can be performed through steps S3 to S9.

Circuit Structure of Optical Sensor

Figure 20:
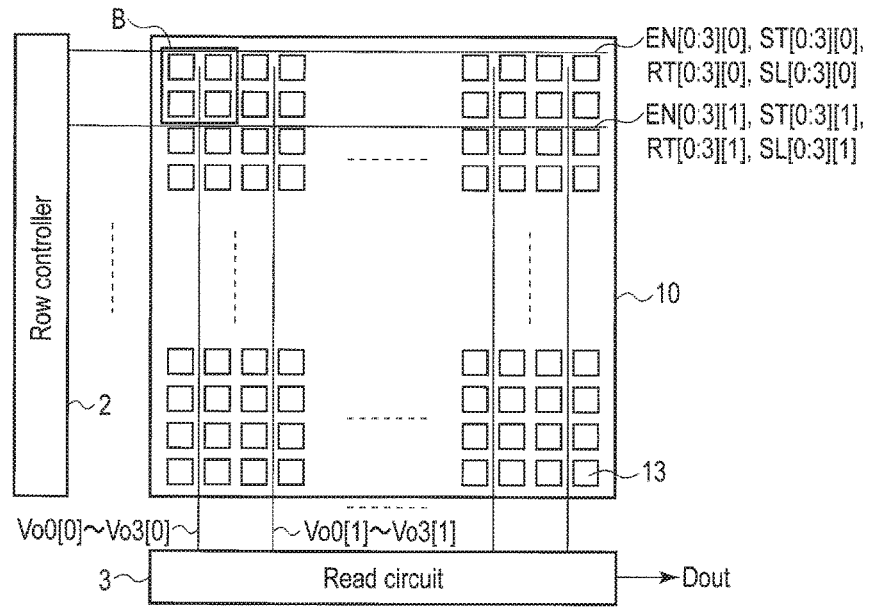
FIG. 20 is a schematic view of an example of a circuit structure of an optical sensor of an embodiment.
Figure 21:
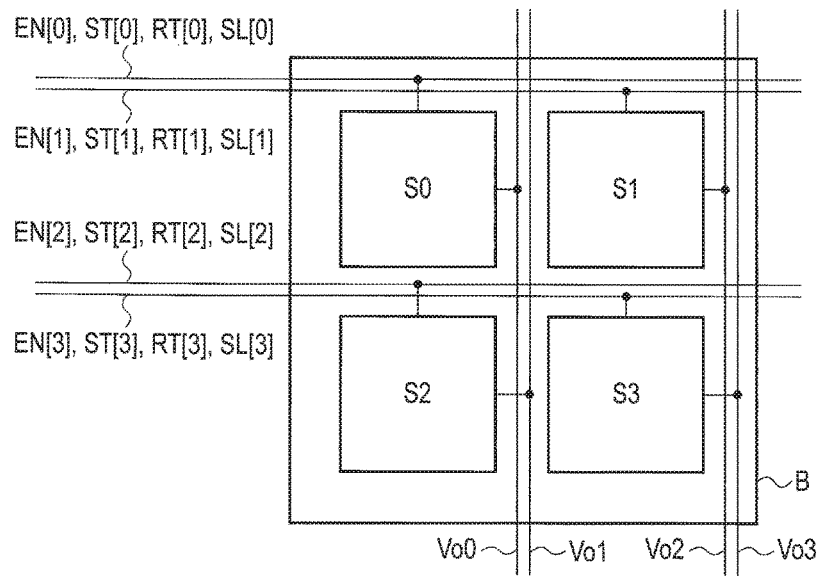
FIG. 21 shows an example of a circuit of an optical sensor element of an optical sensor of an embodiment.

FIGS. 20 and 21 show a schematic example of a circuit structure of an optical sensor of an embodiment.

The optical sensor includes a semiconductor sensor chip 10 with a plurality of sensing parts 13 arranged in a matrix, row controller 2, and read circuit 3.

Several adjacent sensing parts 13 form a basic block B. Therefore, the semiconductor sensor chip 10 includes a plurality of basic blocks B. For example, the basic blocks B each have a similar circuit structure. In this example, one basic block B includes four sensing parts S0, S1, S2 and S3; however, the number of sensing parts 13 in one basic block B is not limited thereto and is any optional number of two or more.

The row controller 2 controls a data detection operation of sensing parts arranged in a matrix. For example, the row controller 2 controls an order of data reading performed by each sensing part.

The row controller 2 outputs, for example, an enable signal EN, stimulation signal ST, reset signal RT and transfer signal SL.

The enable signal EN, stimulation signal ST, reset signal RT and transfer signal SL are applied in common to the basic blocks arranged in the row direction. Here, the enable signal EN, stimulation signal ST, reset signal RT, and transfer signal SL may be supplied from the row controller 2 at different times in each row. More specifically, a signal pattern supplied to a row may be supplied to its next row after being delayed for a certain time.

FIG. 20 shows enable signal EN[0:3][i](i=0, 1, ... ), stimulation signal ST[0:3][i](i=0, 1, ... ), reset signal RT[0:3][i](i=0, 1, ... ), and transfer signal SL[0:3][i](i=0, 1, ... ), and therein, [i](i=0, 1, ... ) indicates the number of the row. In FIG. 21 and its corresponding description, (i=0, 1, ... ) is omitted given that different signals are supplied to the rows at different times.

Given that signals supplied to a basic block B are an enable signal EN[0:3] and a stimulation signal ST[0:3], an enable signal EN[0] and a stimulation signal ST[0] are supplied to sensing part S0, and an enable signal EN[1] and a stimulation signal ST[1] are supplied to sensing part S1. Furthermore, an enable signal EN[2] and a stimulation signal ST[2] are supplied to sensing part S2, and an enable signal EN[3] and a stimulation signal ST[3] are supplied to sensing part S3.

The reset signal RT[0:3] is a signal to reset an input voltage of an amplifier which amplifies a detection signal from a sensing part. The transfer signal SL[0:3] is a signal to transfer an output signal from the amplifier to a read circuit 3.

Given that signals supplied to a basic block B are a reset signal RT[0:3] and a transfer signal SL[0:3], a reset signal RT[0] and a transfer signal SL[0] are supplied to sensing part S0, and a reset signal RT[1] and a transfer signal SL[1] are supplied to sensing part S1. Furthermore, a reset signal RT[2] and a transfer signal SL[2] are supplied to sensing part S2, and a reset signal RT[3] and transfer signal SL[3] are supplied to sensing part S3.

sensing part S0 to S3 send output signals Vo0 to Vo3 to the read circuit 3, respectively.

FIG. 20 shows output signals Vo0[i](i=0, 1, ... ), output signal Vo1[i](i=0, 1, ... ), output signal Vo2[i](i=0, 1, ... ), and output signal Vo3[i](i=0, 1, ... ), and therein, [i](i=0, 1, ... ) indicates the number of the column. In FIG. 20, (i=0, 1, ... ) is omitted given that an output signal is sent to the read circuit 3 column by column.

Figure 22:
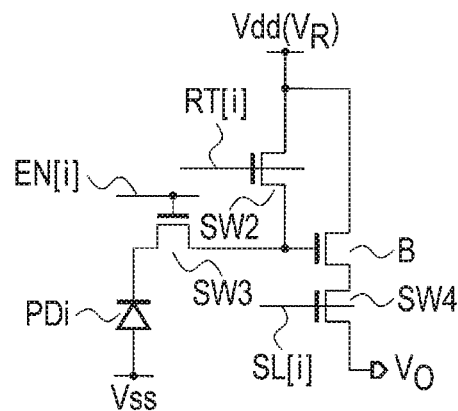
FIG. 22 shows another example of a circuit of an optical sensor element of an optical sensor of an embodiment.

FIG. 22 shows an example of a circuit of a sensing part, and i is an integer of 0 to 3.

The sensing part includes a switch element SW2 configured to reset an input from an amplifier B to a reset voltage VR such as a power voltage Vdd based on a reset signal RT[i], switch element SW3 configured to transfer a detection signal from a photodiode (photoreceptor device) PDi to the amplifier B based on an enable signal EN[i], and switch element SW4 configured to activate an output signal Vo of the amplifier B based on a transfer signal SL[i].

Figure 23:
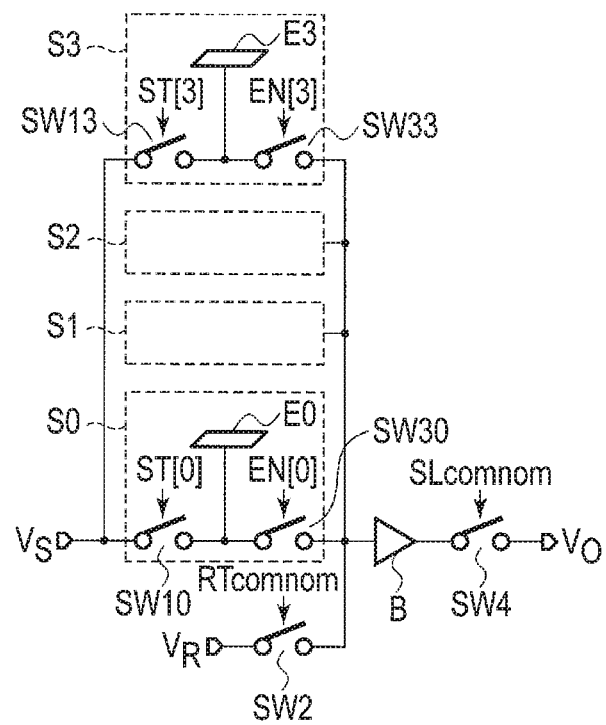
FIG. 23 shows another example of a circuit of an optical sensor element of an optical sensor of an embodiment.

FIG. 23 shows an example of a circuit of a basic block.

In this example, the switch element (reset transistor) SW2 configured to reset the amplifier B and the switch element SW4 configured to activate an output signal of the amplifier B are shared with respect to sensing part S0 to S3 in a basic block B.

The sensing part S0 includes an electrode E0, switch element SW10 configured to apply a stimulation voltage Vs to electrode E0 based on a stimulation signal ST[0], and switch element SW30 configured to transfer a detection signal from electrode E0 to the amplifier B based on an enable signal EN[0].

The sensing part S3 includes an electrode E3, switch element SW13 configured to apply a stimulation voltage Vs to electrode E3 based on a stimulation signal ST[3], and switch element SW33 configured to transfer a detection signal from electrode E3 to the amplifier B based on an enable signal EN[3].

The sensing parts S1 and S2 include, for example, the photodiode PDi and the switch element Sw3 of FIG. 22.

The basic block B includes a switch element SW2 configured to reset an input of the amplifier B to a reset voltage VR based on a common reset signal RTcommon and a switch element SW4 configured to activate an output signal Vo of the amplifier B based on a common transfer signal SLcommon.

The order of data read from each sensing part in such a circuit should be determined arbitrarily.

Furthermore, the above circuit may be connected to each sensing part as a read control circuit which controls signal reading from sensing parts, or several sensing parts are connected to a single circuit, or signal reading may be performed by an operation of a switch. Such a read control circuit may further include a controller configured to control the order of signal reading from sensing parts, and an output circuit which externally outputs the signal from the sensing parts under the control of the controller.

In addition to the read control circuit which controls signal reading from sensing parts, the optical sensor may further include an analog-to-digital conversion circuit if digitization of the signals from the sensing parts is required. Furthermore, in addition to the read control circuit, the optical sensor may include a signal processing circuit configured to process the signals from the sensing parts in accordance with a predetermined order. The signal processing circuit may be referred to as a processing circuit and performs, for example, time quadrature, auto zeroing, chopping, correlated double sampling, and/or correlated multiple sampling. Furthermore, the optical sensor may further include a communication circuit configured to transfer a result obtained therein to an external device, and may further include, on the substrate, a memory circuit configured to store a measurement condition, measurement procedure, correspondence between the result and the sample and/or the obtained result and a power circuit configured to supply power to the optical sensor. The optical sensor may include any of the above circuits individually or in combination.

The optical sensor and the analyzer explained above are used to detect optical data from a contained material (that is, a sample) in the sample container. Through the sensing process by the optical sensor, the optical data of the sample teach information about a target in the sample container. The target may be the entire sample in the sample container or may be a part of the sample in the sample container. If the target is a part of the sample, the target may reside in a medium in the sample container.

The sample is a material which can present optical data when light is irradiated thereonto. The optical data include, for example, absence/presence of light, strength, and/or wavelength. From the optical data, data of the target including, for example, absence/presence, type, distribution, concentration and/or behavior of the target can be acquired.

The sample may be, for example, a biological sample, environmental origin sample, food or beverage origin sample, industrial origin sample, chemical substance or any combination thereof.

The sample has a refractive index which is higher than that of air and may be, for example, a fluid substance, solid substance, viscous substance or any combination thereof.

The target may be, for example, a fluid substance, solid substance, viscous substance, or any combination thereof, by which light hitting thereon scatters in sideways. Or, the target may be a fluid substance, solid substance, or viscous substance including a fluorescence pigment, or may be a fluorescence pigment itself. Specifically, the target can be, for example, a solid substance in a fluid medium, solid substance in a viscous medium, viscous substance in a fluid medium, fluorescence pigment in a fluid medium, fluorescence pigment in a solid medium, fluorescence pigment in a viscous medium or fluorescence pigment in a viscous second medium in a fluid first medium.

The medium is phototransmissive and is, for example, a fluid substance or a viscous substance which does not contain a component producing sideways scattered light or fluorescence having optical data identical to that of the target by light hitting thereon.

Even if the sample does not contain a target with the above-explained characteristics, that is, even if the optical sensor of any one of the embodiments does not detect sideways scattered light or fluorescence, the absence/presence of the sample and/or type may be analyzed by other light reaching sensing parts.

The target can contain, for example, one or more cells. The cell may derive from animal or botanical. Or, the cell can be bacterium, fungus, spore of fungus or virus. The cell can be originated from, for example, biological sample such as a piece of living tissue, isolated cell, cultivated cell, cultivated tissue, cell membrane, blood, blood plasma, serum, urine, feces, and mucosa.

The isolated cell means a cell extracted from a multicellular organism such as an animal or a plant and isolated, or a unicellular organism which is isolated from a multicellular organism or an environment. The cultivated cell means a cell, after the isolation, maintained in a culture medium or in a buffer solution for a certain period of time. The isolated tissue means an isolated tissue extracted from a living body, or an intercellular or extracellular cell component. The isolated tissue may be a piece cut from a larger isolated tissue. The cultivated tissue means the isolated tissue which is maintained in a culture medium or in a buffer solution for a certain period of time.

If the target is a cell, the sample may contain a cell preservation fluid as a medium. The cell preservation fluid has a function to avoid any result-alterable effect to the cell until the analysis starts. The function to avoid any result-alterable effect to the cell means, for example, that the shape of the cell is maintained if the type of the cell is targeted, or that the cell is kept alive if the life/death of the cell is targeted. The cell preservation fluid is, for example, a liquid or a gel. The cell preservation fluid can be, for example, water, physiological saline, buffer solution or any publically-known culture medium.

If the target is a cell, the optical sensor of any of the embodiments can acquire, for example, the absence/presence, life/death, type, distribution, and function of the cell, and distribution, concentration, and behavior of a material related to the target cell.

Method of Analysis

Figure 24:
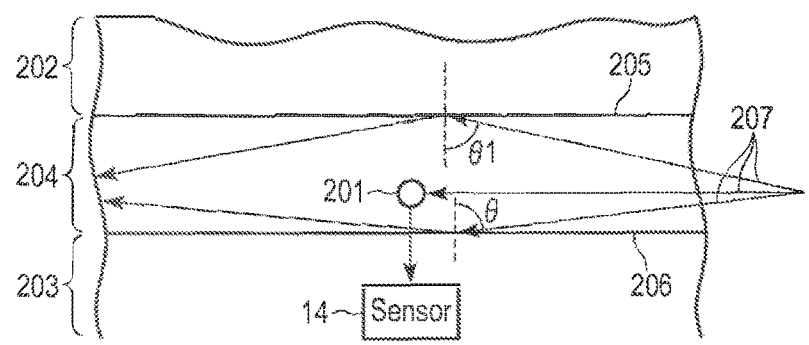
FIG. 24 is a schematic view showing a method of analysis of an embodiment.

According to an embodiment, a method of analysis using the above-described optical sensor or the analyzer can be presented. Hereinafter, the method of analysis will be explained with reference to FIG. 24. FIG. 24 is a schematic view showing the method of analysis.

The method of analysis includes the following steps.

(A) Irradiating light 207 from between an upper surface 205 and a lower surface 206 of a high-refractive-index layer 204 which has a refractive index higher than an upper part 202 and a lower part 203 thereof and includes a target 201 therein, such that the light 207 is incident on the upper part 202 and the lower part 203 of the high-refractive-index layer 204 at an angle greater than or equal to the critical angle and impinges on the target 201.

(B) Detecting light from the target 201 in the lower part 203 of the high-refractive-index layer 204 to obtain optical data associated with positional data.

Each step is detailed.

In step (A), light is irradiated onto the target 201 in the high-refractive-index layer 204. The high-refractive-index layer 204 has a refractive index higher than the upper part 202 and the lower part 203 thereof. The high-refractive-index layer 204 includes a target 201. The target 201 has the aforementioned characteristics. The light is irradiated from between the upper surface 205 and the lower surface 206 of the high-refractive-index layer 204. The light is irradiated at an angle greater than or equal to the greater of the critical angle, angle of incidence 81 at the time when the light is incident on the upper part 202 of the high-refractive-index layer 204, and angle of incidence 8 at the time when the light is incident on the lower part 203 of the high-refractive-index layer 204. Therefore, if the light does not hit the target 201, the light is totally internally reflected by the upper surface 205 and/or the lower part 203 of the high-refractive-index layer 204, stays in the high-refractive-index layer 204, and travels in the opposite side to the light source. The light hitting the target then scatters in sideways. If the target includes a fluorescence pigment, and the light is excitation light of the fluorescence pigment, the target exerts fluorescence upon hit of the light. The sideways scattered light and fluorescence may incident on the lower part 203 of the high-refractive-index layer 204. (B) Detection of light from target and positional data thereof in lower part of layer In step (B), optical data associated with positional data are detected based on the light from the target in step (A). The optical data include aforementioned data. The detection is performed by an optical sensor which is disposed in the lower part 203 of the high-refractive-index layer 204, is opposed to the lower surface 206 of the high-refractive-index layer, and includes the sensor surface 14. The above-described data related to the target can be acquired from the optical data and the positional data.

In some embodiments, the high-refractive-index layer 204 is a combination of a sample contained in the sample container and the bottom. In that case, the light is externally irradiated onto the wall of the sample container at the above angle to pass the wall and be incident on the sample. The light partly impinges on the target. The light which does not hit the target is prevented from passing the bottom. Furthermore, as mentioned above, with the method providing a low-refractive-index layer below the bottom, with the method using the wall with a lens, or with the method using a light blocking film as a part of the wall, the light which fails to hit the target is prevented from passing the bottom more effectively. The light which fails to hit the target may pass the bottom of the sample container and exit the lower part of the high-refractive-index layer. The light which impinges on the target may pass the bottom as sideways scattered light or fluorescence as explained below.

The optical sensor is, for example, the above-described semiconductor sensor chip. In that case, with the method of omitting sensing parts from the region of the semiconductor sensor chip where the scattered light reaches, with the method using a light blocking member which partly shields the sensor surface, or with the method of blocking scattered light by a filter, detection of the light which fails to impinge on the target and passes through the bottom can be prevented.

According to some embodiments, the method of analysis includes the following steps.

(A) Irradiating light onto a sample in a sample container including a target through a phototransmissive wall of the sample container, the sample container including a phototransmissive bottom positioned on or above a sensor surface of an optical sensor to be opposed to a plurality of sensing parts, and the phototransmissive wall arranged to surround the upper surface of the bottom partly or entirely and to extend upward from the circumference of the bottom or from the upper surface of the bottom to an optional height, the phototransmissive wall having a desired thickness.

(B) Receiving light from the target by the sensor surface to obtain optical data associated with positional data of the target.

Example

Figure 25:
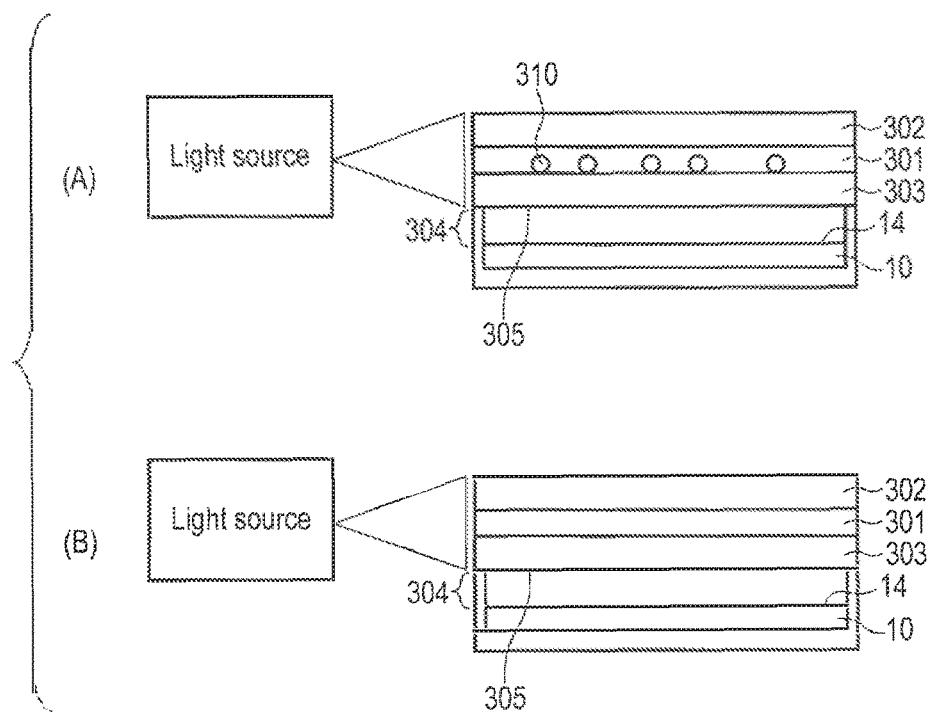
FIG. 25 is a cross-sectional view of the optical sensor used in an example.

An optical sensor of an embodiment was manufactured and used for the analysis. FIG. 25 shows this example.

Initially, beads 310 including fluorescence pigments were prepared as a target and were mixed with water 301. The water 301 including the beads 310 was injected between two glass plates 302 and 303, and this was used as a sample. On the other hand, water 301 was injected between two glasses 302 and 303 and this was used as a comparative sample. The semiconductor sensor chip 10 of FIG. 1 was arranged below each sample with a gap 304 therebetween. The gap between the bottom surface 305 of each sample and the sensor surface 14 of the semiconductor sensor chip 10 was 5 mm. The gap was filled with air. Excitation light of the same wavelength was irradiated from the outside of each sample to the side surface thereof at four different strength grades. After the light of different strength grades was irradiated, the strength of the light detected by the semiconductor sensor chip 10 was measured. FIG. 26 shows a result of the measurement. The light from the sample including the beads showed greater strength than the light from the comparative sample. Fluorescence was visibly observed in the sample including the beads. From the comparative sample, the strength of the light measured was almost 0 lux. This suggests that the excitation light was safely kept in the glass plates and the water and light from the fluorescence pigments in the beads or scattered light from the beads was measured effectively. Thus, it is clear that an optical sensor of an embodiment can acquire optical information about a target.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An optical sensor comprising:
    a plurality of sensing parts two-dimensionally arranged in a matrix to form a sensor surface;
    a phototransmissive sample-supporting plate arranged to be opposed to the sensing parts;
    a phototransmissive wall extending upward from the position enclosing cylindrical surface of surrounding the phototransmissive sample-supporting plate, wherein the phototransmissive wall forms a sample container with the phototransmissive sample-supporting plate as the bottom;
    a light blocking film partly covering side surface of the phototransmissive wall;
    a supporting board fixed to the lower surface of the plurality of sensing parts; and
    an illumination unit comprising a light source fixed to the supporting board;
    wherein the light source is disposed to emit light from the outside of the sample container into the inside thereof through the phototransmissive wall.

2. The optical sensor of claim 1, further comprising a low-refractive-index layer between the sensor surface and the sample-supporting plate.

3. The optical sensor of claim 1, wherein the sample-supporting plate includes a channel therein, and an inside of the channel communicates with an upper part of the bottom through an aperture.

4. An analyzer configured to analyze a target, comprising:
    an optical sensor of claim 1, configured to acquire optical data of a sample containing the target and positional data associated with the optical data;
    an illumination unit configured to emit light to the inside of the sample container from the outside thereof;
    a manipulator; and
    a controller electrically connected to the optical sensor and the manipulator, wherein the controller is configured to determine a region to be treated by the manipulator based on optical data acquired by the optical sensor, positional data associated with the optical data, and threshold conditions predetermined with respect to the optical data and the positional data, and to operate the manipulator in the determined region.

5. The analyzer of claim 4, wherein the optical sensor and the illumination unit are fixed to an upper surface of a supporting plate.

6. An analyzing method comprising:
    (A) irradiating light between an upper surface and a lower surface of a high-refractive-index layer; wherein the high-refractive-index layer has a refractive index higher than an upper part and a lower part; and wherein the upper part and the lower part sandwiches the high-refractive-index layer between thereof; and wherein the high-refractive-index layer includes a target therein, such that the light is incident on the upper surface and the lower surface of the high-refractive-index layer at angles greater than or equal to critical angles and the light impinges on the target; and
    (B) detecting light from the target in the lower part of the high-refractive-index layer to obtain optical data associated with positional data.

* * * * *